US012611449B2

(12) United States Patent
Sahin et al.

(10) Patent No.: US 12,611,449 B2
(45) Date of Patent: Apr. 28, 2026

(54) INDIVIDUALIZED VACCINES FOR CANCER

(71) Applicants: BioNTech SE, Mainz (DE); TRON—Translationale Onkologie an der Universitätsmedizin der Johannes Gutenberg—Universität Mainz gemeinnützige GmbH, Mainz (DE)

(72) Inventors: Ugur Sahin, Mainz (DE); Mathias Vormehr, Mainz (DE); Thomas Bukur, Mainz (DE)

(73) Assignees: BioNTech SE, Mainz (DE); TRON—Translationale Onkologie an der Universitätsmedizin der Johannes Gutenberg-Universität Mainz gemeinnützige GmbH, Mainz (DE)

( * ) Notice: Subject to any disclaimer, the term of this patent is extended or adjusted under 35 U.S.C. 154(b) by 1352 days.

(21) Appl. No.: 17/262,180

(22) PCT Filed: Jul. 23, 2019

(86) PCT No.: PCT/EP2019/069813
§ 371 (c)(1),
(2) Date: Jan. 21, 2021

(87) PCT Pub. No.: WO2020/020894
PCT Pub. Date: Jan. 30, 2020

(65) Prior Publication Data
US 2021/0290746 A1 Sep. 23, 2021

(30) Foreign Application Priority Data
Jul. 24, 2018 (WO) ................ PCT/EP2018/070058

(51) Int. Cl.
*A61K 39/00* (2006.01)
*A61P 35/00* (2006.01)
*C12Q 1/6886* (2018.01)

(52) U.S. Cl.
CPC .... *A61K 39/00119* (2018.08); *A61K 39/0011* (2013.01); *A61K 39/001154* (2018.08); *A61K 39/001156* (2018.08); *A61K 39/001163* (2018.08); *A61P 35/00* (2018.01); *C12Q 1/6886* (2013.01); *A61K 2039/53* (2013.01); *C12Q 2600/158* (2013.01)

(58) Field of Classification Search
CPC ............... A61K 39/00; A61K 2039/53; A61K 39/00119; A61K 39/0011; A61K 2039/70; C12Q 1/6886; C12Q 2600/158
See application file for complete search history.

(56) References Cited

U.S. PATENT DOCUMENTS

| | | | | |
|---|---|---|---|---|
| 10,155,031 B2 * | 12/2018 | Sahin | ................ | A61K 39/0011 |
| 10,738,355 B2 * | 8/2020 | Sahin | ................. | A61P 35/00 |
| 11,156,617 B2 * | 10/2021 | Sahin | ................. | G01N 33/6845 |
| 11,248,264 B2 * | 2/2022 | Sahin | ................. | A61P 37/04 |
| 11,504,419 B2 * | 11/2022 | Sahin | ................. | A61P 35/00 |
| 2015/0125477 A1 * | 5/2015 | Kuttruff-Coqui | .......................... | C07K 16/2833 |
| | | | | 435/320.1 |
| 2016/0101170 A1 * | 4/2016 | Hacohen | ................. | A61P 37/04 |
| | | | | 424/277.1 |
| 2019/0189241 A1 * | 6/2019 | Tadmor | ................. | G16B 20/20 |
| 2022/0074948 A1 * | 3/2022 | Sahin | ................. | A61K 39/0011 |
| 2022/0282322 A1 * | 9/2022 | Sahin | .................... | G16B 40/00 |

FOREIGN PATENT DOCUMENTS

| | | |
|---|---|---|
| WO | WO 2014/144885 A2 | 9/2014 |
| WO | WO 2015/014869 | 2/2015 |
| WO | WO 2017/070618 | 4/2017 |

OTHER PUBLICATIONS

Yamshchikov et al. (Clin. Cancer Res. 2001; 7: 909s-916s).*
Bins et al. (J. Immunother. Feb.-Mar. 2007; 30 (2): 234-239).*
Bodey et al. (Anticancer Res. Jul.-Aug. 2000; 20 (4): 2665-76).*
Lee et al. (J. Immunol. Dec. 1, 1999; 163 (11): 6292-300).*
Zaks et al. (Cancer Res. Nov. 1, 1998; 58 (21): 4902-8).*
Gao et al. (J. Immunother. Nov.-Dec. 2000; 23 (6): 643-53).*
Middleton et al. (Lancet Oncol. Jul. 2014; 15 (8): 829-40).*
Tiraboschi et al. (J. Immunother. Cancer. Dec. 2020; 8 (2): e001535; pp. 1-16).*
Weide et al., "Results of the first phase I/II clinical vaccination trial with direct injection of mRNA", Journal of Immunotherapy, 2008, 31(2), 180-188.
Castle et al., "Immunomic, genomic and transcriptomic characterization of CT26 colorectal carcinoma", BMC Genomics, 2014, 15(1), 12 pages.
Bright et al., "Overexpressed oncogenic tumor-self antigens.", Human Vaccines & Immunotherapeutics 2014, 2014, 10(11), 3297-3305.
Bright et al., "Overexpressed oncogenic tumor-self antigens" Human Vaccines & Immunotherapeutics 2014, vol. 10, No. 11, 2014, pp. 3297-3305.
Castle et al., "Immunomic, genomic and transcriptomic characterization of CT26 colorectal carcinoma", BMC Genomics, vol. 15, No. 1, Mar. 13, 2014 (Mar. 13, 2014), p. 190.

(Continued)

*Primary Examiner* — Peter J Reddig
(74) *Attorney, Agent, or Firm* — McDonnell Boehnen Hulbert & Berghoff LLP

(57) ABSTRACT

The present invention is in the field of tumor immunotherapy. In particular, the present invention provides individualized cancer vaccines specific for a patient's tumor based on a transcriptome analysis in a tumor specimen of the patient for RNA transcripts which are excessively upregulated in one or more cancer cells of said patient. These individualized cancer vaccines when administered to the patient induce an immune response against tumor-associated antigens expressed in a tumor of the patient by the RNA transcripts which are excessively upregulated in one or more cancer cells of said patient. Due to the excessive upregulation of the RNA transcripts, the individualized cancer vaccines are effective for vaccination of a subject and for breaking the self-tolerance against tumor-associated antigens which are self-proteins in said subject.

8 Claims, 16 Drawing Sheets

Specification includes a Sequence Listing.

(56) References Cited

OTHER PUBLICATIONS

Weide et al., "Results of the first phase I/II clinical vaccination trial with direct injection of mRNA", Journal of Immunotherapy, vol. 31, No. 2, Feb. 1, 2008 (Feb. 1, 2008), pp. 180-188.

The International Search Report for International Application No. PCT/EP2018/070058; mailed Apr. 17, 2019, pp. 1-5.

Soria-Guerra et al., "An overview of bioinformatics tools for epitope prediction: Implications on vaccine development." Journal of Biomedical Informatics 53 (2015) 405-414.

* cited by examiner

B16_F10

Day 0    8    15   22         27

RNA lipoplex vaccination    IFNγ ELISpot using splenocytes

Day 0     7     14         19

RNA lipoplex vaccination     IFNγ ELISpot using splenocytes

Fkbp6

Figure 8A                                    CT26
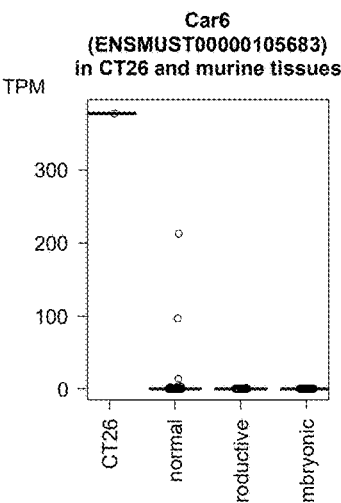
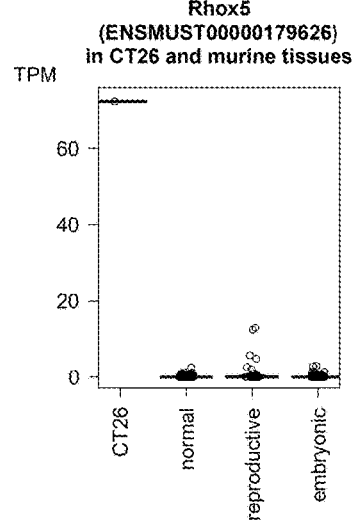
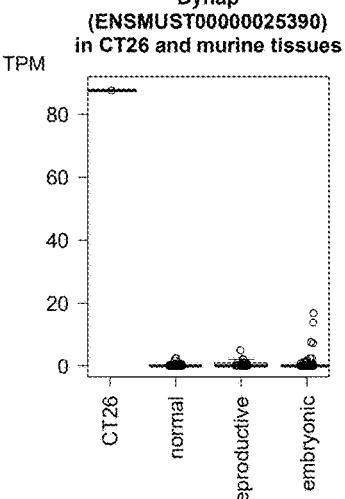
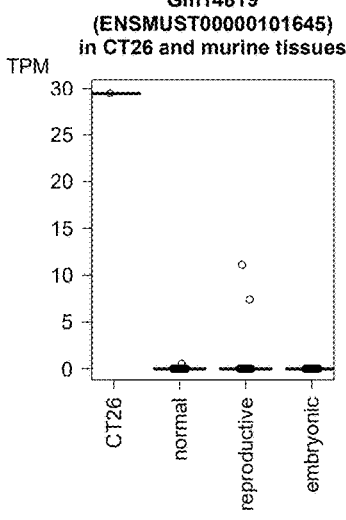
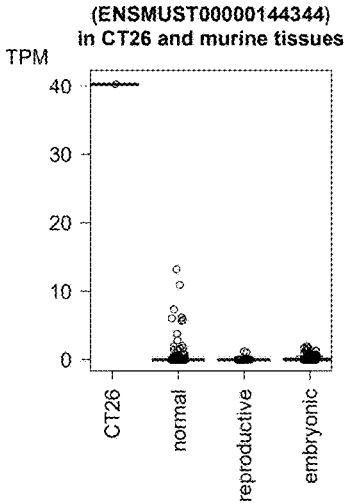
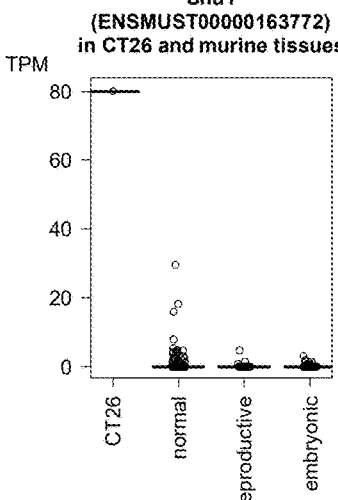
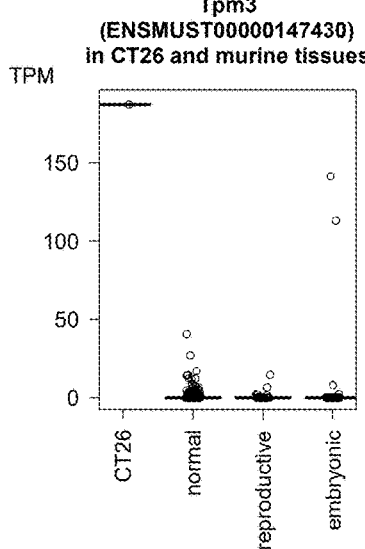

MC38

Figure 8C                    MC38
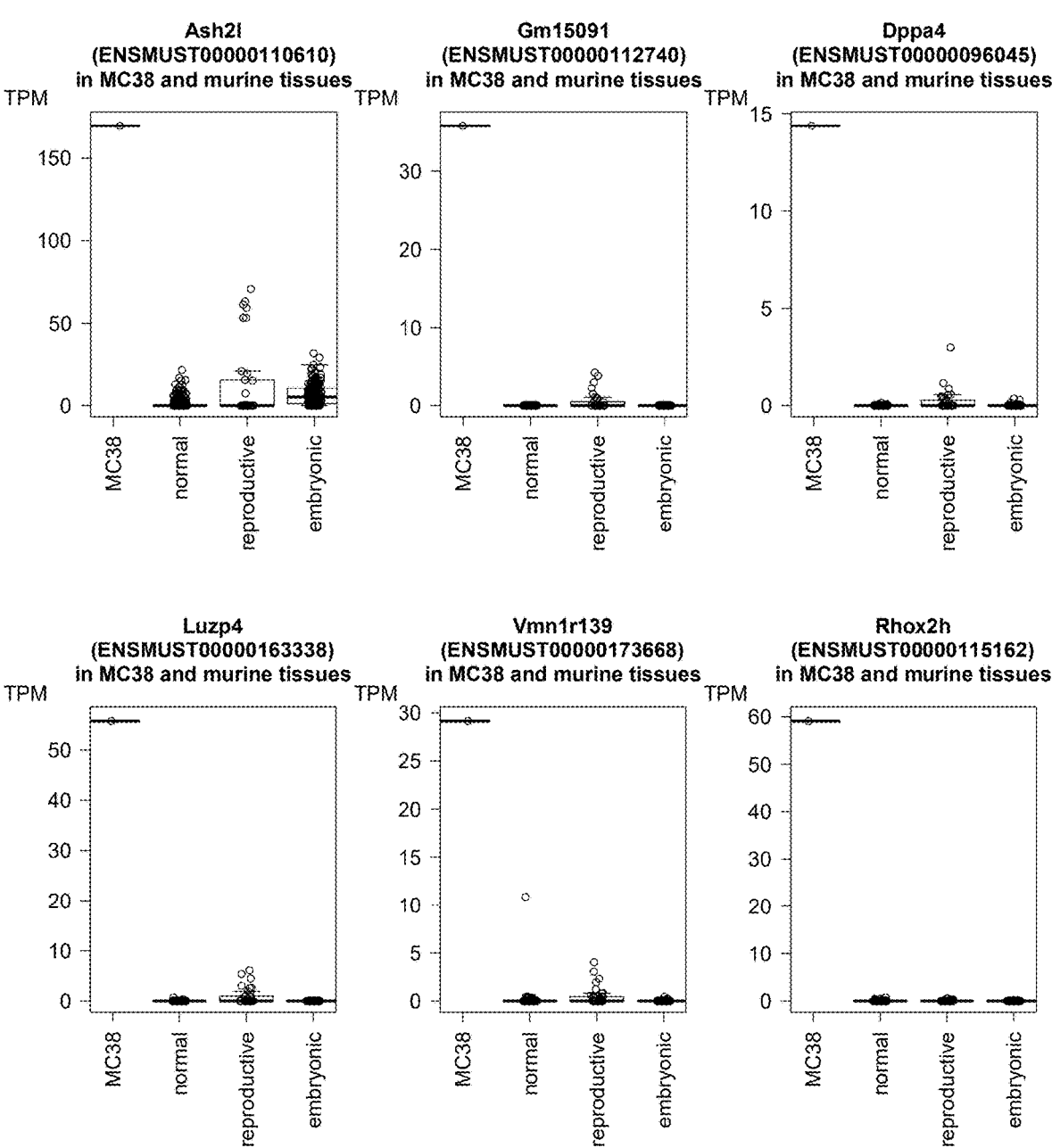

Figure 8D                    TRAMP-C2
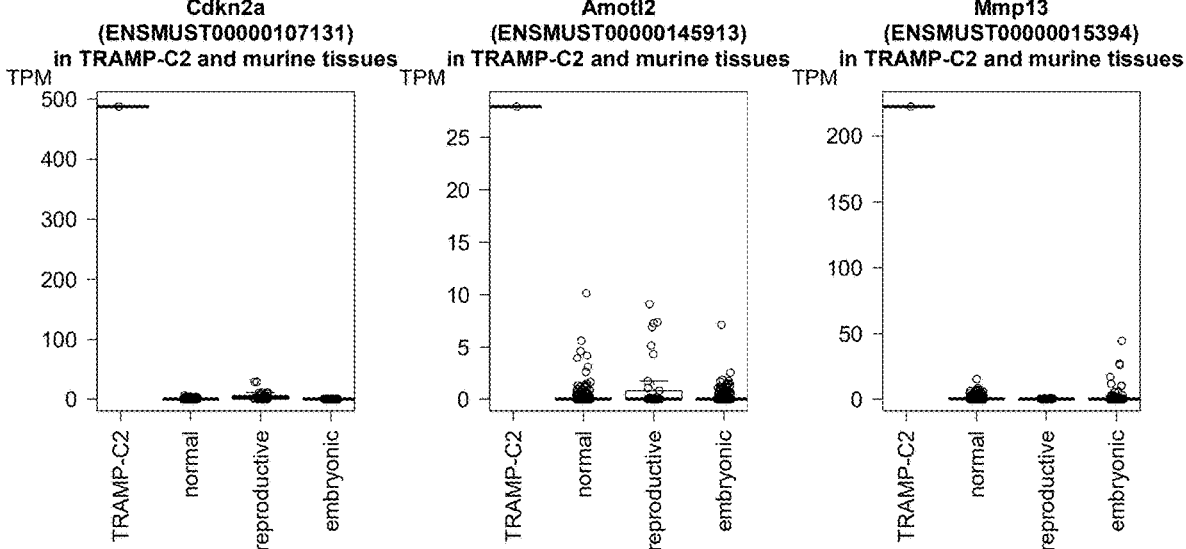

Figure 8E                    4T1
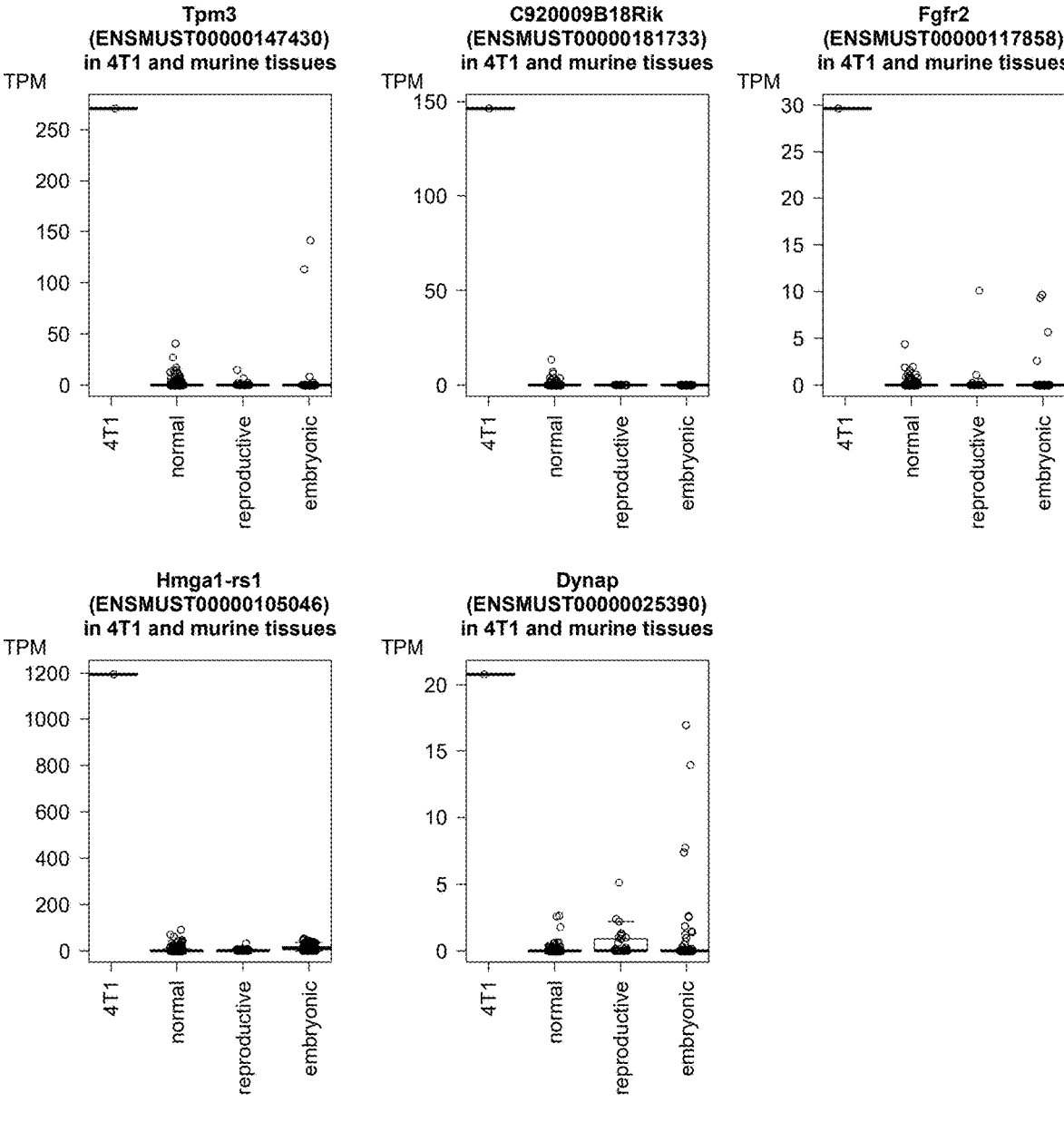

CT26

Day 0    7    14    19

RNA lipoplex vaccination    IFNγ ELISpot using splenocytes

MC38

Day 0     7     14          19

RNA lipoplex vaccination     IFNγ ELISpot using splenocytes

TRAMP-C2

Day 0    7    14    19

RNA lipoplex vaccination    IFNγ ELISpot using splenocytes

INDIVIDUALIZED VACCINES FOR CANCER

CROSS-REFERENCE TO RELATED APPLICATIONS

This application is the US national phase under 35 U.S.C. § 371 of International Application No. PCT/EP2019/069813, filed on Jul. 23, 2019, which claims the benefit of International Application No. PCT/EP2018/070058, filed on Jul. 24, 2018, the contents of which are incorporated herein by reference in their entirety.

SEQUENCE LISTING STATEMENT

The instant application contains an electronic Sequence Listing text file that has been submitted electronically and is hereby incorporated-by-reference in its entirety. The sequence listing was created on Jan. 21, 2021, is named "20-1988-WO-US_Sequence_Listing.txt" and is 2,940 bytes in size.

TECHNICAL FIELD

The present invention is in the field of tumor immunotherapy. In particular, the present invention provides individualized cancer vaccines specific for a patient's tumor based on a transcriptome analysis in a tumor specimen of the patient for RNA transcripts which are excessively upregulated in one or more cancer cells of said patient. These individualized cancer vaccines when administered to the patient induce an immune response against tumor-associated antigens expressed in a tumor of the patient by the RNA transcripts which are excessively upregulated in one or more cancer cells of said patient. Due to the excessive upregulation of the RNA transcripts, the individualized cancer vaccines are effective for vaccination of a subject and for breaking the self-tolerance against tumor-associated antigens which are self-proteins in said subject.

BACKGROUND

Cancer is a primary cause of mortality, accounting for 1 in 4 of all deaths. The treatment of cancer has traditionally been based on the law of averages—what works best for the largest number of patients. However, owing to the molecular heterogeneity in cancer, often less than 25% of treated individuals profit from the approved therapies. Individualized medicine based on tailored treatment of patients is regarded as a potential solution to low efficacies and high costs for innovation in drug development.

Antigen-specific immunotherapy aims to enhance or induce specific immune responses in patients to control malignant diseases. The identification of a growing number of pathogen- and tumor-associated antigens led to a broad collection of suitable targets for immunotherapy. Cells presenting immunogenic peptides (epitopes) derived from these antigens can be specifically targeted by either active or passive immunization strategies. Active immunization tends to induce and expand antigen-specific T cells in the patient, which are able to specifically recognize and kill diseased cells. In contrast passive immunization relies on the adoptive transfer of T cells, which were expanded and optional genetically engineered in vitro (adoptive T cell therapy; ACT).

Tumor vaccines aim to induce endogenous tumor specific immune responses by active immunization. Different antigen formats can be used for tumor vaccination including whole diseased cells, proteins, peptides or immunizing vectors such as RNA, DNA or viral vectors that can be applied either directly in vivo or in vitro by pulsing of DCs following transfer into the patient.

The discovery of multiple pathogen- and tumor-associated antigens has provided the basis for antigen-specific immunotherapy concepts. Tumor-associated antigens (TAA) are unusual proteins expressed on tumor cells due to their genetic instability, which have no or limited expression in normal cells. These TAAs can lead to specific recognition of malignant cells by the immune system. Furthermore, cancers may arise from the accumulation of genomic mutations and epigenetic changes, of which a fraction may have a causative role. In addition to tumor-associated antigens, human cancers carry on average 100-120 non-synonymous mutations, of which many are targetable by vaccines. More than 95% of mutations in a tumor are unique and patient specific. The number of protein changing somatic mutations, which may result in tumor specific T cell epitopes, is in the range of 30 to 400. Mutations are regarded as ideal targets for cancer immunotherapy. As neo-epitopes with strict lack of expression in any healthy tissue, they are expected to be safe and could bypass the central tolerance mechanisms. We have recently proposed a personalized immunotherapy approach targeting the spectrum of individual mutations (Castle, J. C., et al., Cancer Res 72, 1081 (2012)).

In spite of the growing number of attractive target structures for immunotherapeutic approaches the definition of suitable epitopes for immunotherapy remains a challenge. The induction of an immune response against self-proteins requires that immunological self-tolerance is broken.

Self-proteins or peptides thereof are only weakly immunogenic due to immunological tolerance.

Thus, there is a need for providing target structures for vaccination of a cancer patient. These target structures when used in vaccine approaches should, in particular, overcome self-tolerance mechanisms.

SUMMARY

It has been found by the present inventors that many tumors are defined by a characteristic pattern of RNA transcripts. Specifically, specific RNA transcripts are found highly upregulated in specific tumors and individual patients. The present invention is based on the finding that tumors of individual patients have a characteristic transcriptome pattern with excessively upregulated RNA transcripts which are not expressed or expressed in significantly lower amounts in normal healthy cells and tissues of the same and different tissue types. The transcriptome pattern of a tumor makes the tumor unique on the RNA level and distinguishable from non-cancerous tissue, including the corresponding non-cancerous tissue and other non-cancerous tissues. Such unique transcriptome pattern allows the generation of vaccines specifically targeting tumor cells and tumor tissue. The present disclosure relates to the provision of individualized, i.e., patient-specific, cancer vaccines on the basis of tumor-associated antigens encoded by such excessively upregulated RNA transcripts. Specifically, the individualized cancer vaccines provided herein comprise or encode at least one epitope derived from the amino acid sequence(s) encoded by such excessively upregulated RNA transcripts. The present invention aims at immunotherapeutically targeting the expression products of RNA transcripts which are excessively upregulated in tumor cells of a patient, but which are not expressed or expressed in significant lower amounts in non-tumorigenic cells of said patient. Next Generation Sequencing (NGS), for example, allows fast and cost-effective identification of patient specific transcriptome profiles in cancerous cells.

The identification of excessively upregulated transcript species in cancerous cells and the provision of one or more epitopes derived from amino acid sequences encoded by one or more of the excessively upregulated transcript species to the patient by administering a polypeptide comprising the one or more epitopes or a nucleic acid such as RNA encoding the polypeptide with the aim to induce an immune response against said epitopes following appropriate processing of the polypeptide and presentation of the epitopes by MHC molecules for displaying the epitopes to the patient's immune system for stimulating, priming and/or expanding of appropriate T cells which are directed to cancer cells of the patient, provides a novel strategy which is specific for the patient's cancer. Exploiting the transcriptome profile found in circulating tumor cells (CTC) allows for the provision of a vaccine which induces an immune response potentially targeting the primary tumor as well as tumor metastases. Instead of searching for a common molecular denominator for targeting present in many patients, the present invention exploits the characteristic transcriptome profile present in cancer cells of an individual patient.

In one aspect, the invention relates to a method for producing an individualized cancer vaccine comprising the steps:

(a) identifying one or more RNA transcripts present in a tumor specimen of a cancer patient, wherein each of the one or more RNA transcripts encodes an amino acid sequence and wherein each of the one or more RNA transcripts is present in the tumor specimen in a copy number that exceeds a pre-determined expression threshold; and (b) providing a vaccine featuring at least one epitope derived from the amino acid sequence(s) encoded by the one or more RNA transcripts.

In one embodiment, the step of identifying one or more RNA transcripts comprises determining the copy number of RNA transcripts present in a tumor specimen of a cancer patient and comparing the copy number of each of the RNA transcripts to a respective pre-determined expression threshold.

In one embodiment, the copy number of the RNA transcript in the tumor specimen is at least 10 times, preferably at least 1000 times, greater than in non-tumor tissues.

In one embodiment, the copy number of the RNA transcript in the tumor specimen is at least 50, 100, 500, 1000, 2000, 3000, 4000, or 5000 transcripts per million (TPM) and the copy number of the RNA transcript in non-tumor tissues is less than 10%, 5%, 1%, 0.1%, or 0.01% of said copy number of the RNA transcript in the tumor specimen.

In one embodiment, the step of identifying one or more RNA transcripts comprises single cell sequencing of one or more cancer cells.

In one embodiment, the cancer cells are circulating tumor cells.

In one embodiment, the step of identifying one or more RNA transcripts involves using next generation sequencing (NGS).

In one embodiment, the step of identifying one or more RNA transcripts comprises sequencing RNA of the tumor specimen and/or a DNA library obtained from the RNA of the tumor specimen.

In one embodiment, the step of identifying one or more RNA transcripts is replicated at least in duplicates.

In one embodiment, the method comprises the further step of determining the usability of epitopes encoded by the one or more RNA transcripts for cancer vaccination.

In one embodiment, the vaccine comprises a polypeptide comprising one or more epitopes encoded by the one or more RNA transcripts, or a nucleic acid encoding said polypeptide.

In one embodiment, the polypeptide comprises up to 30 epitopes.

In one embodiment, the polypeptide further comprises one or more epitopes not encoded by the one or more RNA transcripts but which are expressed by cancer cells.

In one embodiment, the one or more epitopes not encoded by the one or more RNA transcripts are cancer specific neoepitopes.

In one embodiment, the epitopes are in their natural sequence context so as to form a vaccine sequence.

In one embodiment, the vaccine sequence is about 30 amino acids long.

In one embodiment, the epitopes and/or vaccine sequences are lined up head-to-tail.

In one embodiment, the epitopes and/or vaccine sequences are spaced by linkers.

In one embodiment, the epitopes and/or vaccine sequences have the same amino acid sequence in the tumor specimen as in non-tumor tissues.

In one embodiment, the vaccine is an RNA vaccine.

In one embodiment, the vaccine is a prophylactic and/or therapeutic vaccine.

In a further aspect, the invention relates to an individualized cancer vaccine obtained by the methods described herein.

In a further aspect, the invention relates to an individualized cancer vaccine comprising a recombinant polypeptide comprising epitopes resulting from expression of RNA transcripts in a tumor specimen of a cancer patient, or a nucleic acid encoding said polypeptide, wherein the RNA transcripts are present in the tumor specimen in a copy number that exceeds a pre-determined expression threshold.

In one embodiment, the copy number of the RNA transcript in the tumor specimen is at least 10 times, preferably at least 1000 times, greater than in non-tumor tissues, e.g. non-tumor tissues of the same and different tissue types as the tumor specimen.

In one embodiment, the copy number of the RNA transcript in the tumor specimen is at least 50, 100, 500, 1000, 2000, 3000, 4000, or 5000 transcripts per million (TPM) and the copy number of the RNA transcript in non-tumor tissues is less than 10%, 5%, 1%, 0.1%, or 0.01% of said copy number of the RNA transcript in the tumor specimen.

In one embodiment, the polypeptide further comprises epitopes not encoded by the RNA transcripts but which are expressed by cancer cells.

In a further aspect, the invention relates to a method of treating a cancer patient comprising the steps:

(a) providing an individualized cancer vaccine by the method described herein; and (b) administering the vaccine to the patient.

In a further aspect, the invention relates to a method of treating a cancer patient comprising administering the vaccine described herein to the patient.

In one embodiment, the vaccine is administered intravenously, dermally, muscularly, or subcutaneously.

In one aspect, the present invention relates to a vaccine comprising one or more polypeptides each polypeptide comprising one or more epitopes derived from one or more RNA transcripts which are excessively upregulated in a tumor specimen of a cancer patient, or nucleic acid such as RNA encoding said one or more polypeptides. Preferred embodiments of such vaccine are as described above in the context of the method of the invention.

A vaccine provided according to the invention may comprise a pharmaceutically acceptable carrier and may optionally comprise one or more adjuvants, stabilizers etc. The vaccine may in the form of a therapeutic or prophylactic vaccine.

Another aspect relates to a method for inducing an immune response in a patient, comprising administering to the patient a vaccine provided according to the invention.

In further aspects, the invention provides the vaccines described herein for use in the methods of treatment described herein, in particular for use in treating or preventing cancer.

The treatments of cancer described herein can be combined with surgical resection and/or radiation and/or traditional chemotherapy.

Other features and advantages of the instant invention will be apparent from the following detailed description and claims.

C57BL/6 mice (n=5 per group) were immunized with 40 µg Tyrp1 antigen encoding RNA formulated as lipoplexes or 40 µg irrelevant RNA on days 0, 7 and 14 (see timeline). Five days after the last vaccination, splenocytes of mice were isolated and tested by IFNγ ELISpot for recognition of two Tyrp1 peptides encoding a MHC I epitope (TAP-DNLGYA; SEQ ID NO:3) and MHC II epitope (CRPGWR-GAACNQKI; SEQ ID NO:4), respectively. The mean spot number of triplicates for individual mice (dots) as well as the mean of all mice (bar) is depicted on the left. A picture of the ELISpot plate is shown on the right. Each row represents one mouse.

Figure 3:
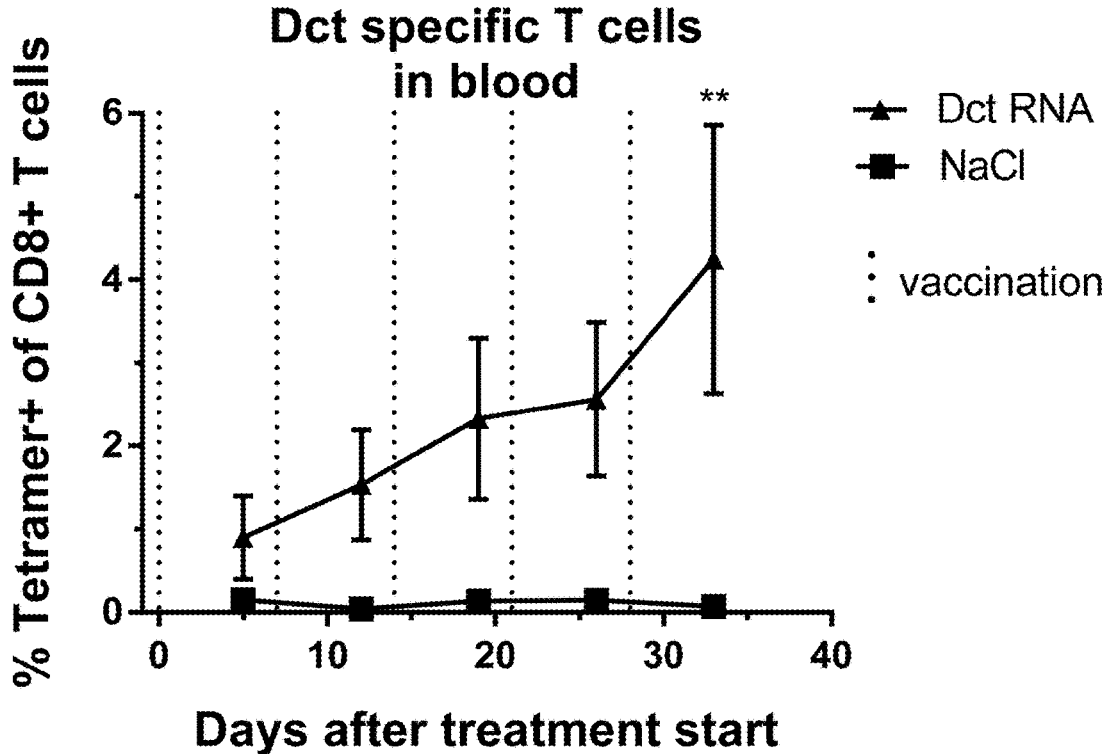

FIG. 3: Immunogenicity testing of a Dct RNA vaccine

C57BL/6 mice (n=5 per group) were repetitively vaccinated with 20 µg Dct encoding RNA lipoplexes or NaCl (vaccination times indicated with dotted lines). On days 5, 12, 19, 26 and 33 after the first vaccination CD8$^+$ T-cell responses against Dct (SVYDFFVWL; SEQ ID NO:5) were measured in blood via MHC tetramer (MBL international) staining by flow cytometry. Depicted is the frequency of Tetramer$^+$ CD8$^+$ T cells among all CD8+ lymphocytes (mean standard error of mean).

Figure 4:
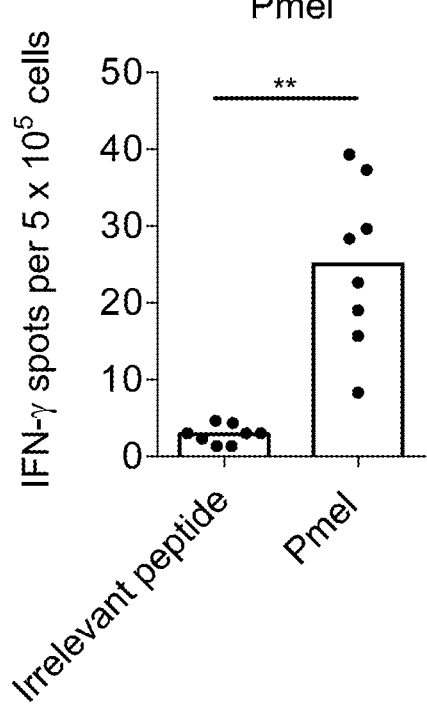

FIG. 4: Immunogenicity testing of a Pmel RNA vaccine

C57BL/6 mice (n=8 per group) were repetitively vaccinated with 20 µg Pmel encoding RNA lipoplexes as shown in the timeline. 27 days after the first vaccination splenocytes of mice were probed against a Pmel peptide (EGSRNQDWL; SEQ ID NO:6) or irrelevant peptide (VSV-NP, RGYVYQGL; SEQ ID NO:7) by IFNγ ELISpot. The mean spot number of triplicates for individual mice (dots) as well as the mean of all mice (bar) is depicted.

Figure 5:
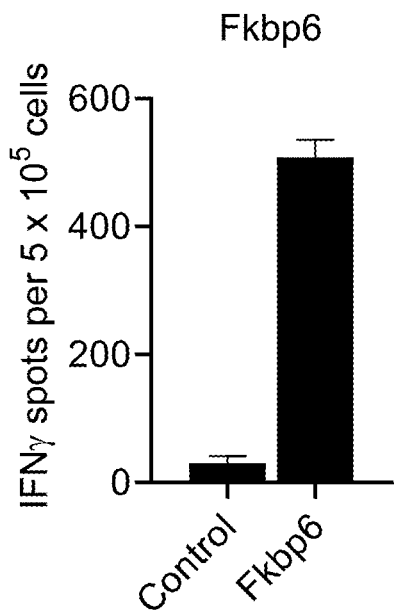

FIG. 5: Immunogenicity testing of a Fkbp6 RNA vaccine

C57BL/6 mice (n=3 per group) were repetitively vaccinated with 20 µg Fkbp6 encoding RNA lipoplexes as shown in the timeline. 5 days after the last vaccination splenocytes of mice were tested for recognition of Fkbp6 RNA or irrelevant RNA (Control) electroporated BMDC by IFNγ ELISpot. The mean spot number plus standard deviation of duplicates (control) or triplicates (Fkbp9) for splenocytes of pooled mice is depicted.

Figure 6:
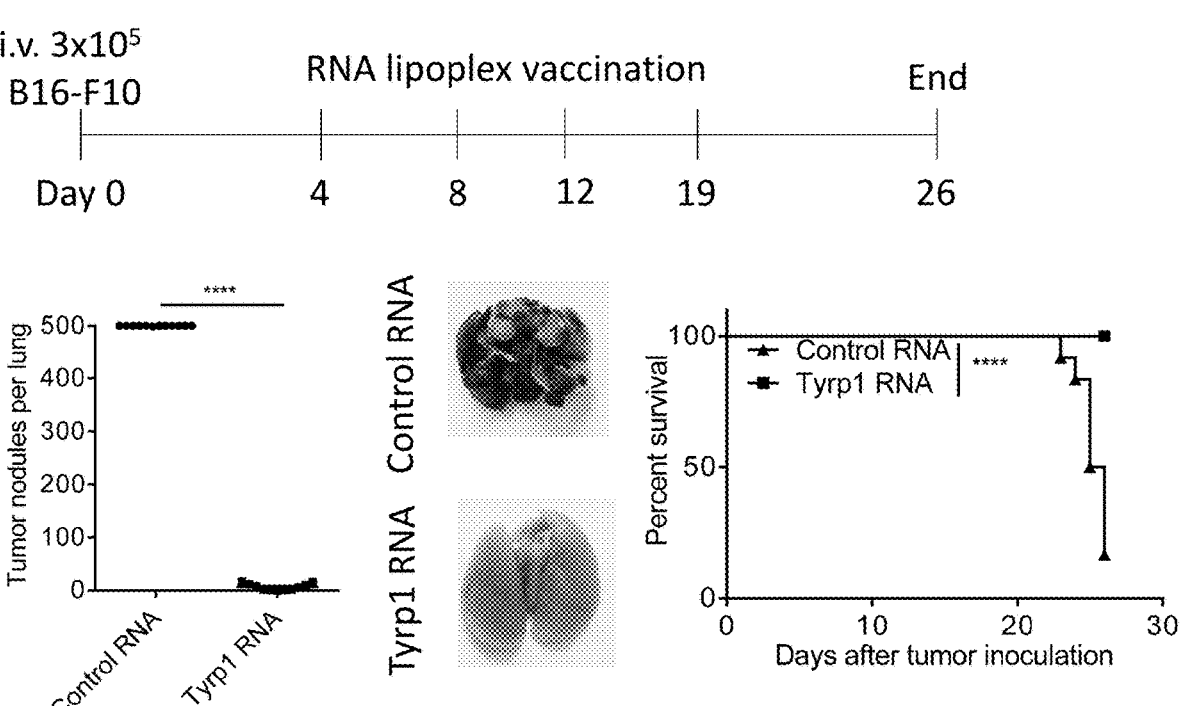

FIG. 6: Tumor control after therapeutic Tyrp1 vaccination

C57BL/6 mice (n=11-12 per group) were inoculated i.v. with $3\times10^5$ B16-F10 tumor cells. RNA lipoplex vaccination with Tyrp1 or irrelevant control RNA was started as shown in the timeline. Lung tumor nodule count per mouse (left), exemplary lungs (middle) and survival (right) is depicted.

Figure 7:
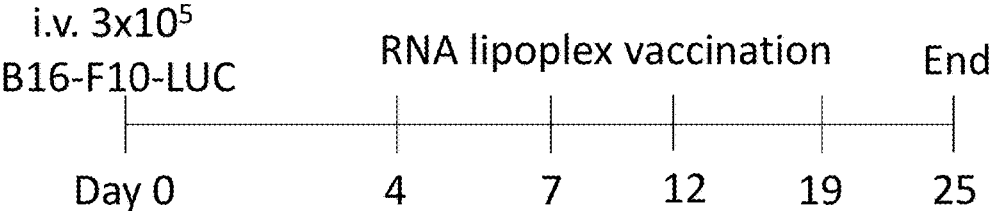
Figure 7:
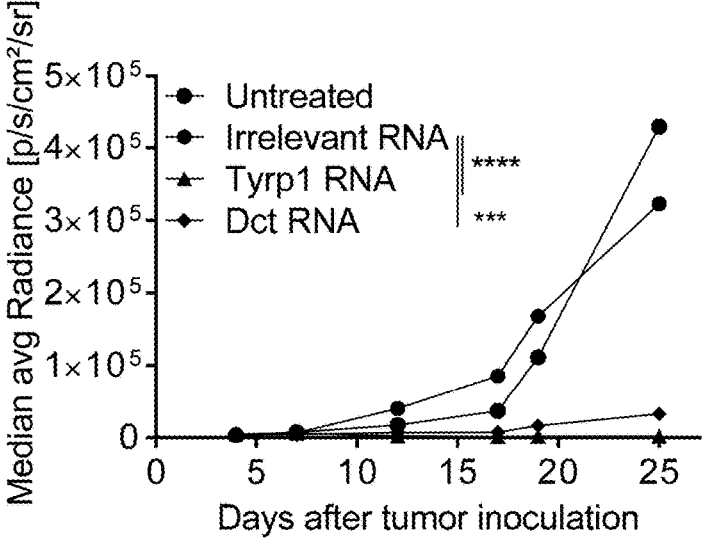
Figure 7:
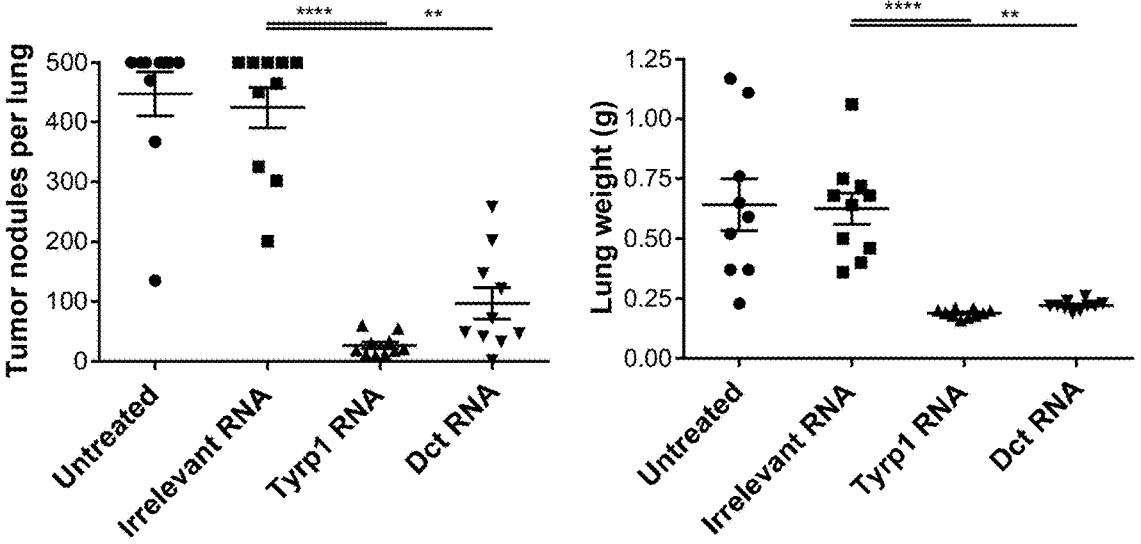
Figure 8B:
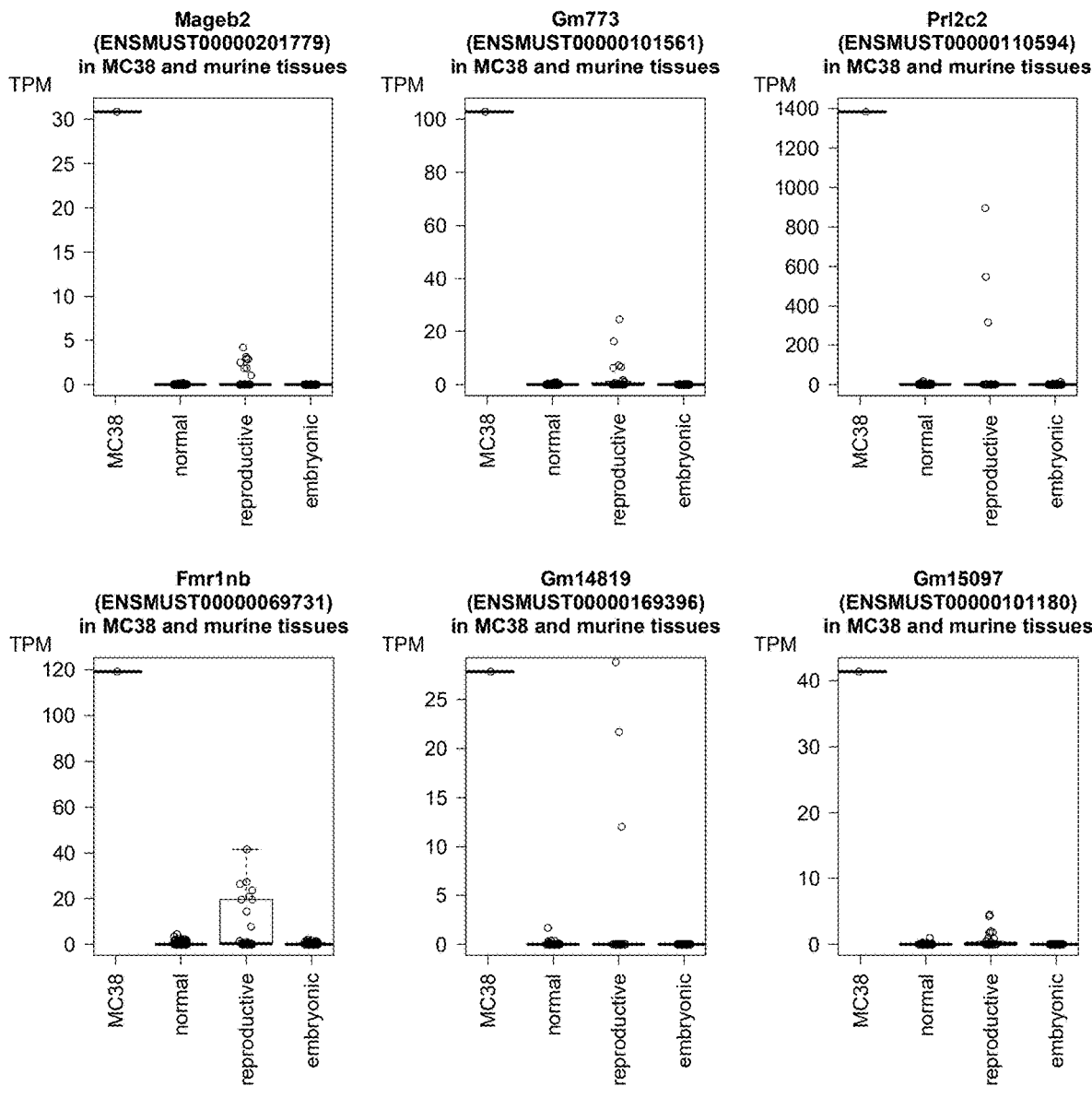

FIG. 7: Tumor control after therapeutic Tyrp1 or Dct vaccination $3\times10^5$ luciferase transgenic B16-F10 tumor cells (B16-F10-LUC) were injected i.v. into naïve C57BL/6 mice (n=12 per group) and treated as depicted in the timeline. Median tumor growth determined by luciferase bioluminescence (left), lung tumor nodule count per mouse (middle, mean±standard error of mean) and lung weight per mouse (right, mean±standard error of mean) is shown.

FIG. 8A-8E: Examples of differentially expressed genes in the tumor models CT26, MC38, TRAMP-C2 and 4T1

Expression values in transcripts per million (TPM) of selected genes in the mouse tumor cell lines CT26 (A), MC38 (B and C), TRAMP-C2 (D) and 4T1 (E) as well as murine tissues subdivided into three classes: normal tissues (n=46), reproductive tissues (n=5), and embryonic tissues (n=14). Tissue expression given as the median of all samples per tissue. Circles indicate single tissue medians. Boxplot center line indicates the median of all tissues, the box depicts the first and the third quartile, whiskers are 2.5-times quartile distance from the median.

Figure 9:
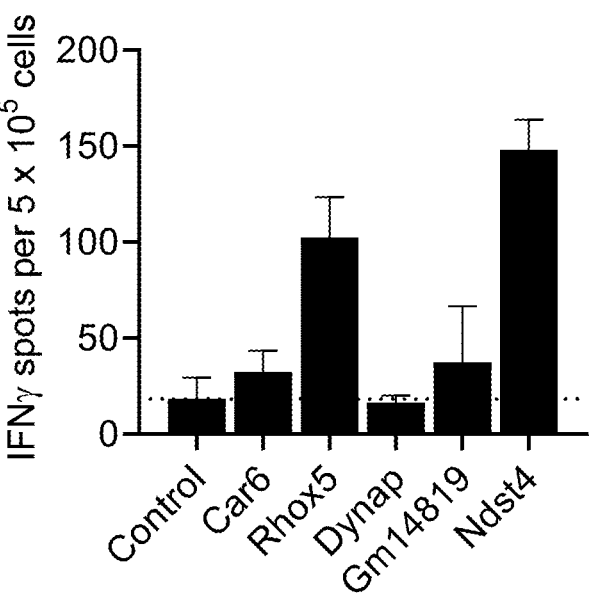

FIG. 9: Immunogenicity testing of targets identified in the CT26 tumor cell line BALB/c mice (n=3 per group) were repetitively vaccinated with 20 µg antigen encoding RNA lipoplexes as shown in the timeline. 5 days after the last vaccination splenocytes of mice were tested for recognition of antigen encoding RNA or irrelevant RNA (Control) electroporated BMDC by IFNγ ELISpot. The mean spot number plus standard deviation of triplicates for splenocytes of pooled mice is depicted.

Figure 10:
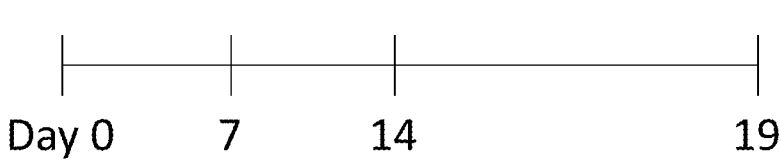
Figure 10:
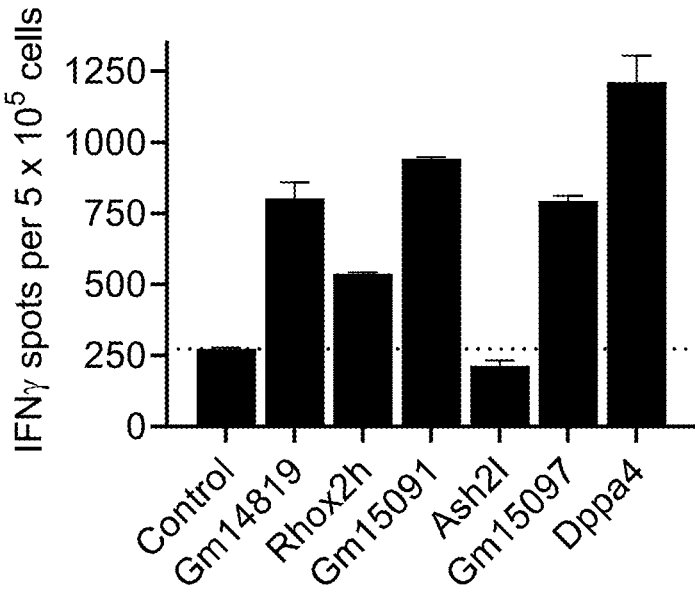
Figure 10:
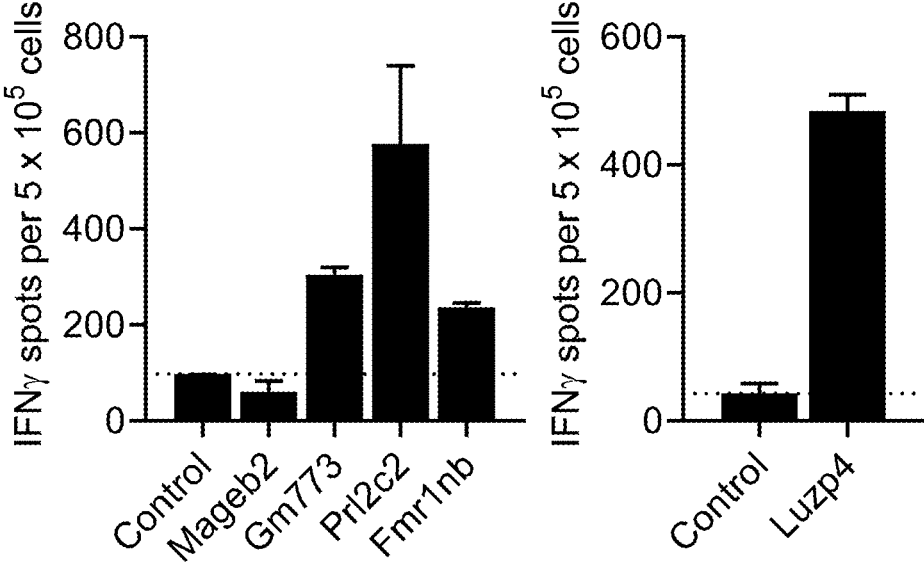

FIG. 10: Immunogenicity testing of targets identified in the MC38 tumor cell line C57BL/6 mice (n=3 per group) were repetitively vaccinated with 20 µg antigen encoding RNA lipoplexes as shown in the timeline. 5 days after the last vaccination splenocytes of mice were tested for recognition of antigen encoding RNA or irrelevant RNA (Control) electroporated BMDC by IFNγ ELISpot. Upper graph, the mean spot number plus standard deviation of duplicates (control) or triplicates (Gm14819, Rhox2h, Gm15091, Ash21, Gm15097, Dppa4) for splenocytes of pooled mice is depicted. Lower graphs, the mean spot number plus standard error of the mean of splenocytes from triplicates of individual mice are shown for the targets Mageb2, Gm773, Prl2c2, Fmrlnb and Luzp4.

Figure 11:
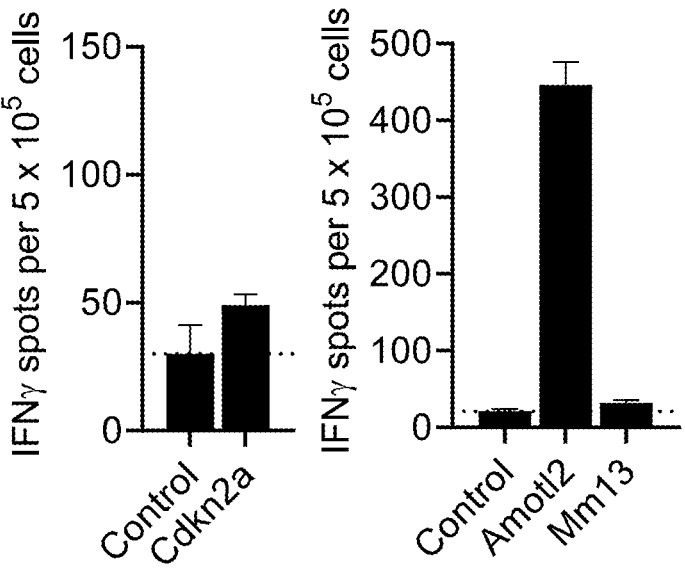

FIG. 11: Immunogenicity testing of targets identified in the TRAMP-C2 tumor cell line C57BL/6 mice (n=3 per group) were repetitively vaccinated with 20 µg antigen encoding RNA lipoplexes as shown in the timeline. 5 days after the last vaccination splenocytes of mice were tested for recognition of antigen encoding RNA or irrelevant RNA (Control) electroporated BMDC by IFNγ ELISpot. The mean spot number plus standard deviation of duplicates (control) or triplicates (antigens) for splenocytes of pooled mice is depicted.

DETAILED DESCRIPTION

Although the present disclosure is described in detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present disclosure will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present disclosure will be described. These elements are listed with specific embodiments, however, it should be understood that they may be combined in any manner and in any number to create additional embodiments. The variously described examples and embodiments should not be construed to limit the present disclosure to only the explicitly described embodiments. This description should be understood to disclose and encompass embodiments which combine the explicitly described embodiments with any number of the disclosed elements. Furthermore, any permutations and combinations of all described elements should be considered disclosed by this description unless the context indicates otherwise.

The term "about" means approximately or nearly, and in the context of a numerical value or range set forth herein in one embodiment means ±20%, ±10%, ±5%, or ±3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

Unless expressly specified otherwise, the term "comprising" is used in the context of the present document to indicate that further members may optionally be present in addition to the members of the list introduced by "comprising". It is, however, contemplated as a specific embodiment of the present disclosure that the term "comprising" encompasses the possibility of no further members being present, i.e. for the purpose of this embodiment "comprising" is to be understood as having the meaning of "consisting of".

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present disclosure was not entitled to antedate such disclosure.

Definitions

In the following, definitions will be provided which apply to all aspects of the present disclosure. The following terms have the following meanings unless otherwise indicated. Any undefined terms have their art recognized meanings.

According to the disclosure, the term "peptide" comprises oligo- and polypeptides and refers to substances which comprise about two or more, about 3 or more, about 4 or more, about 6 or more, about 8 or more, about 10 or more, about 13 or more, about 16 or more, about 20 or more, and up to about 50, about 100 or about 150, consecutive amino acids linked to one another via peptide bonds. The term "protein" or "polypeptide" refers to large peptides, in particular peptides having at least about 151 amino acids, but the terms "peptide", "protein" and "polypeptide" are used herein usually as synonyms.

A "nucleic acid" is according to the invention preferably deoxyribonucleic acid (DNA) or ribonucleic acid (RNA).

In the present disclosure, the term "RNA" relates to a nucleic acid molecule which includes ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally-occurring RNA.

In certain embodiments of the present disclosure, the RNA is messenger RNA (mRNA) that relates to a RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

According to the disclosure, the term "RNA encodes" means that the RNA, if present in the appropriate environment, such as within cells of a target tissue, can direct the assembly of amino acids to produce the peptide or protein it encodes during the process of translation. In one embodiment, RNA is able to interact with the cellular translation machinery allowing translation of the peptide or protein. A cell may produce the encoded peptide or protein intracellularly (e.g. in the cytoplasm and/or in the nucleus), may secrete the encoded peptide or protein, or may produce it on the surface.

A "reference" such as as pre-determined expression threshold may be used to correlate and compare the results obtained in the methods of the invention from a tumor specimen. Typically the "reference" may be obtained on the basis of one or more normal tissues, in particular tissues which are not affected by a tumor or cancer disease (i.e. non-tumor tissues), normally obtained from one or more individuals which are different to a patient from whom a tumor specimen is derived, preferably healthy individuals, in particular individuals of the same species. Non-tumor tissues typically include tissues which are different to the tissue from which a tumor specimen is derived and may include tissue which corresponds to the tissue from which a tumor specimen is derived.

Terms such as "reduce" or "inhibit" as used herein means the ability to cause an overall decrease, for example, of about 5% or greater, about 10% or greater, about 20% or greater, about 50% or greater, or about 75% or greater, in the level. The term "inhibit" or similar phrases includes a complete or essentially complete inhibition, i.e. a reduction to zero or essentially to zero.

Terms such as "increase" or "enhance" in one embodiment relate to an increase or enhancement by at least about 10%, at least about 20%, at least about 30%, at least about 40%, at least about 50%, at least about 80%, or at least about 100%.

The term "recombinant" in the context of the present disclosure means "made through genetic engineering". In one embodiment, a "recombinant object" in the context of the present disclosure is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring. The term "found in nature" means "present in nature" and includes known objects as well as objects that have not yet been discovered and/or isolated from nature, but that may be discovered and/or isolated in the future from a natural source.

The term "Transcripts Per Million" or "TPM" is a normalization method for RNA-seq, and should be read as "for every 1,000,000 RNA molecules in the sample, x came from this gene/transcript."

Excessively Upregulated RNA Transcripts

The present invention relates to a method for producing an individualized cancer vaccine comprising the steps:

(a) identifying one or more RNA transcripts present in a tumor specimen of a cancer patient, wherein each of the one or more RNA transcripts encodes an amino acid sequence and wherein each of the one or more RNA transcripts is present in the tumor specimen in a copy number that exceeds a pre-determined expression threshold; and (b) providing a vaccine featuring at least one epitope derived from the amino acid sequence(s) encoded by the one or more RNA transcripts.

As used herein, the term "expression threshold" relates to a quantitative limit/value that is associated with the level of expression, i.e., the copy number, of an RNA transcript and is to be taken into consideration to carry out the methods described herein. An expression threshold for an RNA transcript is typically characteristic for said RNA transcript. Typically, a level of expression that is below the expression threshold is not considered to reflect excessive upregulation of an RNA transcript (e.g., in tumor or cancer tissue), and in particular is considered to reflect (potential) expression of an RNA transcript in healthy tissue. Typically, a level of expression that is above the expression threshold is considered to reflect excessive upregulation of an RNA transcript (e.g., in tumor or cancer tissue) and, in particular, is not considered to reflect (potential) expression of an RNA transcript in healthy tissue. Thus, the term "expression threshold" refers to the level of expression of an RNA transcript above which the RNA transcript is considered suitable for providing a vaccine featuring at least one epitope derived from the amino acid sequence encoded by the RNA transcript. The expression threshold is typically selected such that expression of the RNA transcript in healthy tissues is not expected at levels which exceed said threshold. Rather, the expression threshold is typically selected such that expression of the RNA transcript in healthy tissues is far below said threshold. A level of expression of said RNA transcript in a diseased tissue such as cancer tissue (e.g. in a tumor specimen) above said expression threshold is typically indicative for the RNA transcript being suitable for providing a vaccine featuring at least one epitope derived from the amino acid sequence encoded by the RNA transcript. The expression threshold is typically determined by obtaining information regarding the level of expression of an RNA transcript in a cohort of (healthy) tissues, preferably tissues of different tissue types, optionally tissues of different subjects, preferably subjects of the same species, and defining the threshold considering the obtained information regarding the level of expression of the RNA transcript. Such cohorts of tissues may include 10 or more such as 100 or more different tissue types. The information regarding the level of expression of the RNA transcript may be obtained, for example, from publicly available databases such as the Sequence Read Archive (SRA). The expression threshold is typically calculated to achieve a useful prediction in terms of effectiveness and/or safety for an RNA transcript being suitable for providing a vaccine featuring at least one epitope derived from the amino acid sequence encoded by the RNA transcript. Typically, the expression threshold is well above the highest level of expression determined for an RNA transcript in healthy tissues and includes a margin of safety; e.g., a certain multiplication factor of the (e.g., highest or median) level of expression determined for an RNA transcript in healthy tissues. Such safety factor may be, for example, 10-fold, 100-fold, or 1000-fold above the level of expression in healthy tissues. Expression thresholds are preferably available in the methods described herein for a number of RNA transcripts, in particular coding transcripts, such as at least 100, at least 1000, or at least 10000 RNA transcripts. Typically, such expression thresholds are pre-determined values, wherein the term "pre-determined" or "pre-defined" designates a constant value which is independent of the determination of an expression level of an RNA transcript in a tumor specimen, i.e., it is not determined when an expression level of an RNA transcript in a tumor specimen is determined, and which is selected as a value to which the expression level of an RNA transcript determined in a tumor specimen has to be compared. Accordingly, an expression threshold is a quantitative value that is associated with and provides information about the level of expression of an RNA transcript in a subject, in particular in different tissues of a subject. In the methods described herein, the level of expression of an RNA transcript in a non-tumor specimen of a subject needs not to be determined and the level of expression of an RNA transcript determined in a tumor specimen of a subject needs not to be compared to the level of expression of the same RNA transcript in a non-tumor specimen of the same subject. Rather, the levels of expression of a number of RNA transcripts (e.g. at least 10, at least 100, at least 1000, or at least 10000 RNA transcripts) are determined in a tumor specimen of a subject and are compared to expression thresholds pre-determined for each of a number of RNA transcripts (e.g. at least 100, at least 1000, or at least 10000 RNA transcripts), e.g. as described above. Accordingly, the methods of the invention may involve the use of a collection of data such as a database comprising information on expression thresholds for a number of RNA transcripts, in particular coding transcripts, such as at least 100, at least 1000, or at least 10000 RNA transcripts. The methods of the invention may involve comparing the level of expression of each of a number of RNA transcripts in a tumor specimen of a subject with a collection of data comprising information on expression thresholds for a number of RNA transcripts to determine whether or not a compared level of expression exceeds the respective expression threshold comprised within the collection of data. Those RNA transcripts the levels of expression of which exceed the respective expression thresholds comprised within the collection of data may be considered as being suitable or potentially suitable for providing a vaccine. In an embodiment, the methods of the present invention can be performed over time until a sufficient number of RNA transcripts considered as being suitable or potentially suitable for providing a vaccine has been obtained. Once this point has been reached, the method can be stopped.

The term "excessively upregulated RNA transcript", "RNA transcript present in the tumor specimen in a copy number that exceeds a pre-determined expression threshold" or similar terms relate to RNA the presence or expression of which in a tumor specimen is strongly increased compared to non-tumor tissues. In various embodiments, the presence or expression of the RNA is at least 10-fold, at least 100-fold, at least $10^3$-fold, at least $10^4$-fold, at least $10^5$-fold or even higher compared to the presence or expression in non-tumor tissues. Preferred according to the invention are those RNA transcripts which are not expressed or are expressed only in low amounts in thymus and/or in critical organs such as heart, brain etc.

In one embodiment, the method of the invention comprises the following steps:

i) providing a tumor specimen from a cancer patient;

ii) identifying excessively upregulated RNA transcripts in the tumor specimen;

iii) designing a polypeptide comprising epitopes of the amino acid sequence(s) encoded by one or more of the excessively upregulated RNA transcripts determined in step (ii);

iv) providing the polypeptide designed in step (iii) or a nucleic acid, preferably RNA, encoding said polypeptide; and v) providing a vaccine comprising the polypeptide or nucleic acid provided in step (iv).

According to the invention, a "tumor specimen" is a sample such as a bodily sample derived from a patient containing or suspected of containing tumor or cancer cells such as circulating tumor cells (CTC), in particular a tissue sample, including body fluids such as blood, and/or a cellular sample, and may be derived from a tumor tissue. In one embodiment, a tumor specimen relates to one or more isolated tumor or cancer cells such as circulating tumor cells (CTCs) or a sample containing one or more isolated tumor or cancer cells such as circulating tumor cells (CTCs).

According to the invention, a "non-tumor tissue" is a tissue which is not affected by a tumor or cancer and which does not contain tumor or cancer cells such as circulating tumor cells (CTC). Bodily samples may be obtained in the conventional manner such as by tissue biopsy, including punch biopsy, and by taking blood, bronchial aspirate, sputum, urine, feces or other body fluids. According to the invention, the term "sample" also includes processed samples such as fractions or isolates of biological samples, e.g. nucleic acid or cell isolates.

The present invention may involve the identification of all excessively upregulated RNA transcripts present in one or more cancer cells of a patient or it may involve the identification of only a portion of the excessively upregulated RNA transcripts present in one or more cancer cells of a patient. Generally, the method of the invention provides for the identification of a number of excessively upregulated RNA transcripts which provides a sufficient number of epitopes to be included into a vaccine.

In context of the present invention, the transcriptome means the set of all RNA molecules, including mRNA, rRNA, tRNA, and other non-coding RNA, produced in a cell, a population of cells, preferably a population of cancer cells, or all cells of a given individual at a certain time point. Thus, the method of the invention may comprise identifying excessively upregulated RNA transcripts of the transcriptome, preferably the entire transcriptome of one or more cancer cells. In one embodiment, the step of identifying excessively upregulated RNA transcripts in a tumor specimen of a cancer patient comprises identifying the transcriptome-wide excessively upregulated RNA transcript profile.

The transcriptome differs from the exome in that it includes only those RNA molecules found in a specified cell or cell population, and may also include the amount or concentration of each RNA molecule in addition to their molecular identities. Unlike the genome, which is roughly fixed for a given cell line (excluding mutations), the transcriptome can vary with external environmental conditions.

In one embodiment, the step of identifying excessively upregulated RNA transcripts comprises single cell sequencing of one or more, preferably 2, 3, 4, 5, 6, 7, 8, 9, 10, 11, 12, 13, 14, 15, 16, 17, 18, 19, 20 or even more cancer cells. Thus, the method of the invention may comprise identifying a transcriptome signature of said one or more cancer cells. In one embodiment, the cancer cells are circulating tumor cells. The cancer cells such as the circulating tumor cells may be isolated prior to single cell sequencing.

In one embodiment, the step of identifying excessively upregulated RNA transcripts involves using next generation sequencing (NGS).

In one embodiment, the step of identifying excessively upregulated RNA transcripts comprises sequencing RNA of a tumor specimen.

To reveal excessively upregulated RNA transcripts the information regarding nature and level of RNA transcripts obtained from the tumor specimen is compared with pre-determined expression thresholds. Such expression thresholds are typically determined for an RNA transcript on the basis of the expression levels thereof in normal non-cancerous cells or tissues. In one embodiment, corresponding information is obtained from a database. In one embodiment, corresponding information includes non-tumor tissues (and the respective RNA expression levels thereof) of more than one tissue type, such as of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 50, or at least 100 tissue types. In one embodiment, corresponding information includes non-tumor tissues (and the respective RNA expression levels thereof) of all tissue types available, e.g. for which RNA expression levels are available in a database. In one embodiment, corresponding information includes non-tumor tissues (and the respective RNA expression levels thereof) of one or more critical organs such as one or more, preferably all of lung, heart, brain, CNS, kidney and liver. In one embodiment, excessive upregulation of a RNA transcript in a tumor specimen versus non-tumor tissues of one or more, preferably all of such critical organs is required, and preferably the RNA transcript in non-tumor specimens of such critical organs is not expressed or not significantly expressed. In one embodiment, corresponding information excludes non-tumor tissues (and the respective RNA expression levels thereof) of one or more reproductive organs such as one or more, preferably all of testis, ovary and placenta. In one embodiment, excessive upregulation of a RNA transcript in a tumor specimen versus non-tumor tissues of one or more, preferably all of such reproductive organs is not required.

Any suitable method may be used to determine excessively upregulated RNA transcripts in a tumor specimen of a cancer patient. Generally, such method comprises determining the partial or complete transcriptome profile, i.e., the relative or absolute amount of one or more transcripts of tumor tissue or of tumor cells of a cancer patient. Such transcriptome profile is then assessed with respect to dysregulated or excessively upregulated RNA species.

The study of transcriptomics (which includes expression profiling, splice variant analysis etc.) examines the expression level of transcripts in a given cell population, often focusing on mRNA, but sometimes including others such as tRNAs, sRNAs.

Transcriptomics technologies are the techniques used to study an organism's transcriptome, the sum of all of its RNA transcripts. The information content of an organism is recorded in the DNA of its genome and expressed through transcription. Here, mRNA serves as a transient intermediary molecule in the information network, whilst non-coding RNA performs additional diverse functions. A transcriptome captures a snapshot in time of the total transcripts present in a cell. The first attempts to study the whole transcriptome began in the early 1990s, and technological advances since the late 1990s have made transcriptomics a widespread discipline. There are two key contemporary techniques in the field: microarrays, which quantify a set of predetermined sequences, and RNA-Seq, which uses high-throughput sequencing to capture all sequences. Transcription can also be studied at the level of individual cells by single-cell transcriptomics.

Microarrays

Microarrays that measure the abundances of a defined set of transcripts via their hybridization to an array of complementary probes were first published in 1995. Microarray technology allowed to assay thousands of transcripts simultaneously, at a greatly reduced cost per gene and labor saving. Both spotted oligonucleotide arrays and Affymetrix high-density arrays were the method of choice for transcriptional profiling until the late 2000s. Over this period, a range of microarrays was produced to cover known genes in model or economically important organisms. Advances in design and manufacture of arrays improved the specificity of probes and allowed more genes to be tested on a single array. Advances in fluorescence detection increased the sensitivity and measurement accuracy for low abundance transcripts.

RNA-Seq

RNA-Seq refers to the sequencing of transcript cDNAs, where abundance is derived from the number of counts from each transcript. The technique has therefore been heavily influenced by the development of high-throughput sequencing technologies. Massively Parallel Signature Sequencing (MPSS) was an early example based on generating 16-20 bp sequences via a complex series of hybridizations and was used in 2004 to validate the expression of ten thousand genes in *Arabidopsis thaliana*. The earliest RNA-Seq work was published in 2006 with one hundred thousand transcripts sequenced using the 454 technology. This was sufficient coverage to quantify relative transcript abundance. RNA-Seq began to increase in popularity after 2008 when new Solexa/Illumina technologies allowed one billion transcript sequences to be recorded. This yield now allows to quantify and compare human transcriptomes.

Public Available Transcriptome Databases

The function of most genes is not yet known. A search of a transcriptome database can give researchers a list of all the tissues in which a gene is expressed, providing clues about its possible function. For example, if the transcriptome database shows that an unknown gene's expression levels are dramatically higher in cancer cells than in healthy cells, the unknown gene may play a role in cell growth. The transcriptome data provide the skilled person with the relevant information to identify excessively upregulated RNA transcripts in cancerous cells. The National Human Genome Research Institute (NHGRI), which is part of the National Institutes of Health (NIH), has participated in two projects that created transcriptome resources for researchers around the world: the Mammalian Gene Collection initiative and the Mouse Transcriptome Project. The Mammalian Gene Collection initiative built a free, public library of human, mouse, and rat mRNA sequences and may serve as a suitable database within the context of the present invention. The project was led by NHGRI and the National Cancer Institute (NCI), also part of NIH. Mouse and rat are important models for studying human biology. The Mouse Transcriptome Project was an NIH-supported initiative that generated a free, public database of gene transcripts for many mouse tissues and may serve as a suitable database within the context of the present invention. These tissue-specific gene expression data, which are mapped to the mouse genome, are available in a searchable format in the Mouse Reference Transcriptome Database. Several other transcriptome resources exist, including those in NIH programs such as the Genotype-Tissue Expression Project (GTEx) and the Encyclopedia of DNA Elements (ENCODE) all of which may serve as a suitable database within the context of the present invention. Thereby, GTEx is creating a catalog of human gene expression in a variety of different tissues. ENCODE researchers aim to characterize and understand the working parts of the genome, including the transcriptome. Both Novartis and the European Molecular Biology Laboratory have well-established gene expression databases all of which may serve as a suitable database within the context of the present invention.

A number of organism-specific transcriptome databases have been constructed and annotated to aid in the identification of genes that are differentially expressed in distinct cell populations all of which may serve as a suitable database within the context of the present invention.

RNA-Seq is emerging as the method of choice for measuring transcriptomes of organisms, though the older technique of DNA microarrays is still used. According to the invention, RNA-Seq is preferably used for identifying excessively upregulated RNA transcripts.

Any suitable sequencing method can be used according to the invention, Next Generation Sequencing (NGS) technologies being preferred. Third Generation Sequencing methods might substitute for the NGS technology in the future to speed up the sequencing step of the method. For clarification purposes: the terms "Next Generation Sequencing" or "NGS" in the context of the present invention mean all novel high throughput sequencing technologies which, in contrast to the "conventional" sequencing methodology known as Sanger chemistry, read nucleic acid templates randomly in parallel along the entire genome by breaking the entire genome into small pieces. Such NGS technologies (also known as massively parallel sequencing technologies) are able to deliver nucleic acid sequence information of a whole genome, exome, transcriptome (all transcribed sequences of a genome) or methylome (all methylated sequences of a genome) in very short time periods, e.g. within 1-2 weeks, preferably within 1-7 days or most preferably within less than 24 hours and allow, in principle, single cell sequencing approaches. Multiple NGS platforms which are commercially available or which are mentioned in the literature can be used in the context of the present invention e.g. those described in detail in Zhang et al. 2011: *The impact of next-generation sequencing on genomics. J Genet Genomics* 38 (3), 95-109; or in Voelkerding et al. 2009: *Next generation sequencing: From basic research to diagnostics. Clinical chemistry* 55, 641-658. Non-limiting examples of such NGS technologies/platforms are 1) The sequencing-by-synthesis technology known as pyrosequencing implemented e.g. in the GS-FLX 454 Genome Sequencer™ of Roche-associated company 454 Life Sciences (Branford, Connecticut), first described in Ronaghi et al. 1998: *A sequencing method based on real-time pyrophosphate". Science* 281 (5375), 363-365. This technology uses an emulsion PCR in which single-stranded DNA binding beads are encapsulated by vigorous vortexing into aqueous micelles containing PCR reactants surrounded by oil for emulsion PCR amplification. During the pyrosequencing process, light emitted from phosphate molecules during nucleotide incorporation is recorded as the polymerase synthesizes the DNA strand.

2) The sequencing-by-synthesis approaches developed by Solexa (now part of Illumina Inc., San Diego, California) which is based on reversible dye-terminators and implemented e.g. in the Illumina/Solexa Genome Analyzer™ and in the Illumina HiSeq 2000 Genome Analyzer™. In this technology, all four nucleotides are added simultaneously into oligo-primed cluster fragments in flow-cell channels along with DNA polymerase. Bridge amplification extends cluster strands with all four fluorescently labeled nucleotides for sequencing.

3) Sequencing-by-ligation approaches, e.g. implemented in the SOLid™ platform of Applied Biosystems (now Life Technologies Corporation, Carlsbad, California). In this technology, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting bead, each containing only copies of the same DNA molecule, are deposited on a glass slide. As a second example, he Polonator™ G.007 platform of Dover Systems (Salem, New Hampshire) also employs a sequencing-by-ligation approach by using a randomly arrayed, bead-based, emulsion PCR to amplify DNA fragments for parallel sequencing.

4) Single-molecule sequencing technologies such as e.g. implemented in the PacBio RS system of Pacific Biosciences (Menlo Park, California) or in the HeliScope™ platform of Helicos Biosciences (Cambridge, Massachusetts). The distinct characteristic of this technology is its ability to sequence single DNA or RNA molecules without amplification, defined as Single-Molecule Real Time (SMRT) DNA sequencing. For example, HeliScope uses a highly sensitive fluorescence detection system to directly detect each nucleotide as it is synthesized. A similar approach based on fluorescence resonance energy transfer (FRET) has been developed from Visigen Biotechnology (Houston, Texas). Other fluorescence-based single-molecule techniques are from U.S. Genomics (GeneEngine™) and Genovoxx (AnyGene™).

5) Nano-technologies for single-molecule sequencing in which various nanostructures are used which are e.g. arranged on a chip to monitor the movement of a polymerase molecule on a single strand during replication. Non-limiting examples for approaches based on nano-technologies are the GridON™ platform of Oxford Nanopore Technologies (Oxford, UK), the hybridization-assisted nano-pore sequencing (HANS™) platforms developed by Nabsys (Providence, Rhode Island), and the proprietary ligase-based DNA sequencing platform with DNA nanoball (DNB) technology called combinatorial probe-anchor ligation (cPAL™)

6) Electron microscopy based technologies for single-molecule sequencing, e.g. those developed by Light-Speed Genomics (Sunnyvale, California) and Halcyon Molecular (Redwood City, California)

7) Ion semiconductor sequencing which is based on the detection of hydrogen ions that are released during the polymerisation of DNA. For example, Ion Torrent Systems (San Francisco, California) uses a high-density array of micro-machined wells to perform this biochemical process in a massively parallel way. Each well holds a different DNA template. Beneath the wells is an ion-sensitive layer and beneath that a proprietary Ion sensor.

RNA preparations may serve as starting material for NGS. Such nucleic acids can be easily obtained from samples such as biological material, e.g. from fresh, flash-frozen or formalin-fixed paraffin embedded tumor tissues (FFPE) or from freshly isolated cells or from CTCs which are present in the peripheral blood of patients.

According to the invention, a high-throughput genome-wide single cell genotyping method can be applied. Such approach may comprise the following steps:

1. Obtaining a tumor specimen from a given patient.
2. Extracting the transcriptome (RNA) from the tumor cells, converting it into cDNA and sequencing to determine amounts of transcripts expressed by the tumor cells.
3. Identification of excessively upregulated RNA transcripts.

Vaccine

A vaccine for cancer treatment described herein features at least one epitope derived from the amino acid sequence(s) encoded by one or more excessively upregulated RNA transcripts. In one embodiment, the vaccine comprises a polypeptide comprising one or more epitopes encoded by one or more excessively upregulated RNA transcripts. In one embodiment, the vaccine comprises a nucleic acid, in particular RNA, encoding a polypeptide comprising one or more epitopes encoded by one or more excessively upregulated RNA transcripts.

Accordingly, for vaccination, one or more epitopes of excessively upregulated RNA transcripts are provided to a patient in the form of a polypeptide comprising the one or more epitopes, or a nucleic acid, in particular RNA, encoding the polypeptide. Such polypeptide may be monoepitopic or polyepitopic. Furthermore, such polypeptide may correspond to the tumor-associated antigen expressed by an excessively upregulated RNA transcript or may be a recombinant polypeptide, e.g. a polypeptide comprising epitopes derived from one or more tumor-associated antigen(s) expressed by excessively upregulated RNA transcript(s). The nucleic acid may be translated in cells of the patient, in particular antigen presenting cells, to produce the polypeptide. Following appropriate processing of the polypeptide by cells, the epitopes are presented by MHC and displayed to the patient's immune system for stimulation of appropriate T cells.

A vaccine provided according to the methods of the present invention relates to a vaccine which when administered to a patent preferably provides a collection of MHC presented epitopes, such as 2 or more, 5 or more, 10 or more, 15 or more, 20 or more, 25 or more, 30 or more and preferably up to 60, up to 55, up to 50, up to 45, up to 40, up to 35 or up to 30 MHC presented epitopes, which MHC presented epitopes are derived from amino acid sequences encoded by excessively upregulated RNA transcripts. Presentation of these epitopes by cells of a patient, in particular antigen presenting cells, preferably results in T cells targeting the epitopes when bound to MHC and thus, the patient's tumor, preferably the primary tumor as well as tumor metastases, expressing antigens from which the MHC presented epitopes are derived and presenting the same epitopes on the surface of the tumor cells.

For providing a vaccine, the method of the invention may comprise the arbitrary inclusion of a sufficient number of epitopes encoded by one or more cancer specific excessively upregulated RNA transcripts (preferably in the form of an encoding nucleic acid) into a vaccine or it may comprise the further step of determining the usability of the excessively upregulated RNA transcripts and/or epitopes for cancer vaccination. Thus further steps can involve one or more of the following: (i) prioritizing or ranking the excessively upregulated RNA transcripts, for example according to the level of excessive upregulation; in general, the more excessively upregulated an RNA transcript the better it is suited for providing a vaccine, (ii) assessing whether the amino acid sequences encoded by the excessively upregulated RNA transcripts contain known or predicted MHC presented epitopes, (iii) in vitro and/or in silico testing whether the amino acid sequences encoded by the excessively upregulated RNA transcripts contain MHC presented epitopes, e.g. testing whether the amino acid sequences encoded by the excessively upregulated RNA transcripts contain sequences which are processed into and/or presented as MHC presented epitopes, and (iv) in vitro testing whether the envisaged epitopes, in particular when present in their natural sequence context, e.g. when flanked by amino acid sequences also flanking said epitopes in the naturally occurring protein, and when expressed in antigen presenting cells are able to stimulate T cells of the patient having the desired specificity. Such flanking sequences each may comprise 3 or more, 5 or more, 10 or more, 15 or more, 20 or more and preferably up to 50, up to 45, up to 40, up to 35 or up to 30 amino acids and may flank the epitope sequence N-terminally and/or C-terminally.

The step of identifying epitopes which are potentially immunogenic may comprise determining and/or ranking epitopes according to a prediction of their MHC-binding capacity, preferably MHC class-I binding capacity.

The collection of epitopes identified according to the invention and provided by a vaccine of the invention is preferably present in the form of a polypeptide comprising said epitopes (polyepitopic or multiepitopic polypeptide) or a nucleic acid, in particular RNA, encoding said polypeptide. In certain embodiments of the present disclosure, the polypeptide comprises at least two epitopes, at least three epitopes, at least four epitopes, at least five epitopes, at least six epitopes, at least seven epitopes, at least eight epitopes, at least nine epitopes, or at least ten epitopes being derived from the same or different tumor-associated antigens encoded by excessively upregulated RNA transcripts. The epitopes may be present in the polypeptide in the form of a vaccine sequence, i.e. present in their natural sequence context, e.g. flanked by amino acid sequences also flanking the epitopes in the naturally occurring protein. Such flanking sequences each may comprise 3 or more, 5 or more, 10 or more, 15 or more, 20 or more and preferably up to 50, up to 45, up to 40, up to 35 or up to 30 amino acids and may flank the epitope sequence N-terminally and/or C-terminally. Thus, a vaccine sequence may comprise 20 or more, 25 or more, 30 or more, 35 or more, 40 or more and preferably up to 50, up to 45, up to 40, up to 35 or up to 30 amino acids. In one embodiment, the epitopes and/or vaccine sequences are lined up in the polypeptide head-to-tail.

In one particularly preferred embodiment, a polyepitopic or multiepitopic polypeptide according to the present invention is administered to a patient in the form of a nucleic acid, preferably RNA such as in vitro transcribed or synthetic RNA, which may be expressed in cells of a patient such as antigen presenting cells to produce the polypeptide.

In one embodiment, the epitopes and/or vaccine sequences are spaced by linkers, in particular neutral linkers. The term "linker" according to the invention relates to a peptide added between two peptide domains such as epitopes or vaccine sequences to connect said peptide domains. There is no particular limitation regarding the linker sequence. However, it is preferred that the linker sequence reduces steric hindrance between the two peptide domains, is well translated, and supports or allows processing of the epitopes. Furthermore, the linker should have no or only little immunogenic sequence elements. Linkers preferably should not create non-endogenous epitopes like those generated from the junction suture between adjacent epitopes, which might generate unwanted immune reactions. Therefore, the polyepitopic vaccine should preferably contain linker sequences which are able to reduce the number of unwanted MHC binding junction epitopes. Hoyt et al. (EMBO J. 25(8), 1720-9, 2006) and Zhang et al. (J. Biol. Chem., 279(10), 8635-41, 2004) have shown that glycine-rich sequences impair proteasomal processing and thus the use of glycine rich linker sequences act to minimize the number of linker-contained peptides that can be processed by the proteasome. Furthermore, glycine was observed to inhibit a strong binding in MHC binding groove positions (Abastado et al., J. Immunol. 151(7), 3569-75, 1993). Schlessinger et al. (Proteins, 61(1), 115-26, 2005) had found that the amino acids glycine and serine included in an amino acid sequence result in a more flexible protein that is more efficiently translated and processed by the proteasome, enabling better access to the encoded epitopes. The linker each may comprise 3 or more, 6 or more, 9 or more, 10 or more, 15 or more, 20 or more and preferably up to 50, up to 45, up to 40, up to 35 or up to 30 amino acids. Preferably the linker is enriched in glycine and/or serine amino acids. Preferably, at least 50%, at least 60%, at least 70%, at least 80%, at least 90%, or at least 95% of the amino acids of the linker are glycine and/or serine. In one preferred embodiment, a linker is substantially composed of the amino acids glycine and serine. In one embodiment, the linker comprises the amino acid sequence $(GGS)_a(GSS)_b(GGG)_c(SSG)_d$ $(GSG)_e$ (SEQ ID NO:1) wherein a, b, c, d and e is independently a number selected from 0, 1, 2, 3, 4, 5, 6, 7, 8, 9, 10, 11, 12, 13, 14, 15, 16, 17, 18, 19, or 20 and wherein a+b+c+d+e are different from 0 and preferably are 2 or more, 3 or more, 4 or more or 5 or more. In one embodiment, the linker comprises the sequence GGSGGGGSG (SEQ ID NO:2).

In another embodiment of the present invention the collection of epitopes identified according to the invention and provided by a vaccine of the invention is preferably present in the form of a collection of polypeptides comprising said epitopes on different polypeptides, wherein said polypeptides each comprise one or more epitopes, which can also be overlapping, or a collection of nucleic acids, in particular RNAs, encoding said polypeptides. In the case of an administration of more than one polyepitopic and/or multiepitopic polypeptide the epitopes provided by the different polypeptides may be different or partially overlapping.

Once present in cells of a patient such as antigen presenting cells the polypeptide according to the invention is processed to produce the epitopes identified according to the invention. Administration of a vaccine provided according to the invention may provide MHC class II-presented epitopes that are capable of eliciting a CD4+ helper T cell response against cells expressing antigens from which the MHC presented epitopes are derived. Alternatively or additionally, administration of a vaccine provided according to the invention may provide MHC class I-presented epitopes that are capable of eliciting a CD8+ T cell response against cells expressing antigens from which the MHC presented epitopes are derived. Preferably, a vaccine provided according to the invention is useful for polyepitopic stimulation of cytotoxic and/or helper T cell responses.

A polypeptide comprising one or more epitopes, or a nucleic acid, in particular RNA, encoding the polypeptide described herein used for vaccination preferably results in stimulation, priming and/or expansion of T cells in the subject being administered the polypeptide or nucleic acid. Said stimulated, primed and/or expanded T cells are preferably directed against a target antigen, in particular a target antigen expressed by cancer cells, tissues and/or organs, i.e., a tumor-associated antigen expressed by an excessively upregulated RNA transcript. Thus, a polypeptide comprising one or more epitopes may comprise the tumor-associated antigen, or a fragment thereof (e.g., an epitope or vaccine sequence), or may comprise a variant of the tumor-associated antigen or fragment thereof. In one embodiment, such variant is immunologically equivalent to the tumor-associated antigen or fragment. In the context of the present disclosure, the term "variant of a tumor-associated antigen or fragment thereof" means a sequence which results in stimulation, priming and/or expansion of T cells which stimulated, primed and/or expanded T cells target the tumor-associated antigen, in particular when presented by diseased cells, tissues and/or organs. Thus, the polypeptide comprising one or more epitopes may correspond to or may comprise the tumor-associated antigen, may correspond to or may comprise a fragment of the tumor-associated antigen or may correspond to or may comprise an amino acid sequence which is homologous to the tumor-associated antigen or a fragment thereof. If the polypeptide comprising one or more epitopes comprises a fragment of the tumor-associated antigen or an amino acid sequence which is homologous to a fragment of the tumor-associated antigen said fragment or amino acid sequence may comprise an epitope such as a T cell epitope of the tumor-associated antigen or a sequence which is homologous to an epitope such as a T cell epitope of the tumor-associated antigen. Thus, according to the disclosure, a polypeptide comprising one or more epitopes may comprise an immunogenic fragment of a tumor-associated antigen encoded by an excessively upregulated RNA transcript or an amino acid sequence being homologous to an immunogenic fragment of a tumor-associated antigen encoded by an excessively upregulated RNA transcript. An "immunogenic fragment of an antigen" according to the disclosure preferably relates to a fragment of an antigen which is capable of stimulating, priming and/or expanding T cells when presented in the context of MHC molecules. It is preferred that the polypeptide comprising one or more epitopes (similar to the tumor-associated antigen) can be presented by a cell such as an antigen-presenting cell so as to provide the relevant epitope for binding by T cells.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present disclosure, the term "immunologically equivalent" is preferably used with respect to the immunological effects or properties of antigens or antigen variants used for immunization. For example, an amino acid sequence is immunologically equivalent to a reference amino acid sequence if said amino acid sequence when exposed to the immune system of a subject, such as T cells binding to the reference amino acid sequence or cells expressing the reference amino acid sequence, induces an immune reaction having a specificity of reacting with the reference amino acid sequence. Thus, a molecule which is immunologically equivalent to an antigen exhibits the same or essentially the same properties and/or exerts the same or essentially the same effects regarding stimulation, priming and/or expansion of T cells as the antigen to which the T cells are targeted.

In one embodiment, a vaccine described herein comprises one or more tumor-associated antigens encoded by (a) excessively upregulated RNA transcript(s) or one or more nucleic acids, in particular one or more RNAs, encoding (a) tumor-associated antigen(s). In one embodiment, a vaccine described herein comprises two or more tumor-associated antigens encoded by excessively upregulated RNA transcripts or two or more nucleic acids, in particular two or more RNAs, encoding tumor-associated antigens. In different embodiments, two or more includes 3 or more, 4 or more, 5 or more, 6 or more, 7 or more, 8 or more, 9 or more, or 10 or more. The two or more tumor-associated antigens or nucleic acids may be present in a mixture or may be present separate from each other in a vaccine and consequently may be administered separate from each other, e.g. at different time points and/or by different routes, to a patient.

The term "priming" refers to a process wherein a T cell has its first contact with its specific antigen and causes differentiation into effector T cells.

The term "clonal expansion" or "expansion" refers to a process wherein a specific entity is multiplied. In the context of the present disclosure, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

The peptide or polypeptide encoded by an excessively upregulated RNA transcript is also termed "tumor-associated antigen" or "tumor antigen" herein. In one embodiment, the peptide or polypeptide encoded by an excessively upregulated RNA transcript may be a "standard" antigen, which does not differ in its amino acid sequence between cancer tissue and healthy tissue. Alternatively or additionally, the peptide or polypeptide encoded by an excessively upregulated RNA transcript may be a "neo-antigen", which is specific to an individual's tumor and has not been previously recognized by the immune system. A neo-antigen or neo-epitope may result from one or more cancer-specific mutations in the genome of cancer cells resulting in amino acid changes. For purposes of the present disclosure, however, an excessively upregulated RNA transcript encoding a standard antigen and the corresponding excessively upregulated RNA transcript encoding a neo-antigen are considered the same transcript and contribute both to the amount or copy number of the excessively upregulated RNA transcript.

Cancer mutations vary with each individual. Thus, cancer mutations that encode novel epitopes (neo-epitopes) represent attractive targets in the development of vaccine compositions and immunotherapies. The efficacy of tumor immunotherapy relies on the selection of cancer-specific antigens and epitopes capable of inducing a potent immune response within a host.

The term "mutation" refers to a change of or difference in the nucleic acid sequence (nucleotide substitution, addition or deletion) compared to a reference. A "somatic mutation" can occur in any of the cells of the body except the germ cells (sperm and egg) and therefore are not passed on to children. These alterations can (but do not always) cause cancer or other diseases. Preferably, a mutation is a non-synonymous mutation. The term "non-synonymous mutation" refers to a mutation, preferably a nucleotide substitution, which does result in an amino acid change such as an amino acid substitution in the translation product.

According to the invention, the term "mutation" includes point mutations, Indels, fusions, chromothripsis and RNA edits.

According to the invention, the term "Indel" describes a special mutation class, defined as a mutation resulting in a colocalized insertion and deletion and a net gain or loss in nucleotides. In coding regions of the genome, unless the length of an Indel is a multiple of 3, they produce a frameshift mutation. Indels can be contrasted with a point mutation; where an Indel inserts and deletes nucleotides from a sequence, a point mutation is a form of substitution that replaces one of the nucleotides.

Fusions can generate hybrid genes formed from two previously separate genes. It can occur as the result of a translocation, interstitial deletion, or chromosomal inversion. Often, fusion genes are oncogenes. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. Oncogenic fusion transcripts may also be caused by trans-splicing or read-through events.

According to the invention, the term "chromothripsis" refers to a genetic phenomenon by which specific regions of the genome are shattered and then stitched together via a single devastating event.

According to the invention, the term "RNA edit" or "RNA editing" refers to molecular processes in which the information content in an RNA molecule is altered through a chemical change in the base makeup. RNA editing includes nucleoside modifications such as cytidine (C) to uridine (U) and adenosine (A) to inosine (I) deaminations, as well as non-templated nucleotide additions and insertions. RNA editing in mRNAs effectively alters the amino acid sequence of the encoded protein so that it differs from that predicted by the genomic DNA sequence.

The term "antigen" relates to an agent comprising an epitope against which an immune response can be generated. The term "antigen" includes, in particular, proteins and peptides. In one embodiment, an antigen is presented by cells of the immune system such as antigen presenting cells like dendritic cells or macrophages. An antigen or a processing product thereof such as a T cell epitope is in one embodiment bound by a T or B cell receptor, or by an immunoglobulin molecule such as an antibody. Accordingly, an antigen or a processing product thereof may react specifically with antibodies or T-lymphocytes (T-cells). In one embodiment, an antigen is a disease-associated antigen, such as a tumor antigen, a viral antigen, or a bacterial antigen and an epitope is derived from such antigen.

The term "tumor-associated antigen" is used in its broadest sense to refer to any antigen associated with a tumor or with cancer. A tumor-associated antigen is preferably encoded by an excessively upregulated RNA transcript and may be a molecule which contains epitopes that will stimulate a host's immune system to make a cellular antigen-specific immune response and/or a humoral antibody response against the tumor or cancer. The tumor-associated antigen or an epitope thereof may therefore be used for therapeutic purposes.

The term "epitope" refers to a part or fragment a molecule such as an antigen that is recognized by the immune system. For example, the epitope may be recognized by T cells, B cells or antibodies. An epitope of an antigen may include a continuous or discontinuous portion of the antigen and may be between about 5 and about 100, such as between about 5 and about 50, more preferably between about 8 and about 30, most preferably between about 10 and about 25 amino acids in length, for example, the epitope may be preferably 9, 10, 11, 12, 13, 14, 15, 16, 17, 18, 19, 20, 21, 22, 23, 24, or 25 amino acids in length. In one embodiment, an epitope is between about 10 and about 25 amino acids in length. The term "epitope" includes T cell epitopes.

As used herein the term "neo-epitope" refers to an epitope that is not present in a reference such as a normal non-cancerous or germline cell but is found in cancer cells. This includes, in particular, situations wherein in a normal non-cancerous or germline cell a corresponding epitope is found, however, due to one or more mutations in a cancer cell the sequence of the epitope is changed so as to result in the neo-epitope.

The term "T cell epitope" refers to a part or fragment of a protein that is recognized by a T cell when presented in the context of MHC molecules.

The term "major histocompatibility complex" and the abbreviation "MHC" includes MHC class I and MHC class II molecules and relates to a complex of genes which is present in all vertebrates. MHC proteins or molecules are important for signaling between lymphocytes and antigen presenting cells or diseased cells in immune reactions, wherein the MHC proteins or molecules bind peptide epitopes and present them for recognition by T cell receptors on T cells. The proteins encoded by the MHC are expressed on the surface of cells, and display both self-antigens (peptide fragments from the cell itself) and non-self-antigens (e.g., fragments of invading microorganisms) to a T cell. In the case of class I MHC/peptide complexes, the binding peptides are typically about 8 to about 10 amino acids long although longer or shorter peptides may be effective. In the case of class II MHC/peptide complexes, the binding peptides are typically about 10 to about 25 amino acids long and are in particular about 13 to about 18 amino acids long, whereas longer and shorter peptides may be effective.

The terms "T cell" and "T lymphocyte" are used interchangeably herein and include T helper cells (CD4+ T cells) and cytotoxic T cells (CTLs, CD8+ T cells) which comprise cytolytic T cells. The term "antigen-specific T cell" or similar terms relate to a T cell which recognizes the antigen to which the T cell is targeted, in particular when presented on the surface of antigen presenting cells or diseased cells such as cancer cells in the context of MHC molecules and preferably exerts effector functions of T cells. T cells are considered to be specific for antigen if the cells kill target cells expressing an antigen. T cell specificity may be evaluated using any of a variety of standard techniques, for example, within a chromium release assay or proliferation assay. Alternatively, synthesis of lymphokines (such as interferon-γ) can be measured.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable e.g. by translation of a truncated open reading frame that lacks the 3'-end of the open reading frame. A fragment shortened at the N-terminus (C-terminal fragment) is obtainable e.g. by translation of a truncated open reading frame that lacks the 5'-end of the open reading frame, as long as the truncated open reading frame comprises a start codon that serves to initiate translation. A fragment of an amino acid sequence comprises e.g. at least 50%, at least 60%, at least 70%, at least 80%, at least 90% of the amino acid residues from an amino acid sequence. A fragment of an amino acid sequence preferably comprises at least 6, in particular at least 8, at least 12, at least 15, at least 20, at least 30, at least 50, or at least 100 consecutive amino acids from an amino acid sequence.

For the purposes of the present disclosure, "variants" of an amino acid sequence (peptide or protein) comprise amino acid insertion variants, amino acid addition variants, amino acid deletion variants and/or amino acid substitution variants. The term "variant" includes all splice variants, post-translationally modified variants, conformations, isoforms and species homologs, in particular those which are naturally expressed by cells.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid addition variants comprise amino- and/or carboxy-terminal fusions of one or more amino acids, such as 1, 2, 3, 5, 10, 20, 30, 50, or more amino acids. Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the disclosure at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

In one embodiment, a fragment or variant of an amino acid sequence (peptide or protein) is preferably a "functional fragment" or "functional variant". The term "functional fragment" or "functional variant" of an amino acid sequence relates to any fragment or variant exhibiting one or more functional properties identical or similar to those of the amino acid sequence from which it is derived, i.e., it is functionally equivalent.

An amino acid sequence (peptide or protein) "derived from" a designated amino acid sequence (peptide or protein) refers to the origin of the first amino acid sequence. Preferably, the amino acid sequence which is derived from a particular amino acid sequence has an amino acid sequence that is identical, essentially identical or homologous to that particular sequence or a fragment thereof. Amino acid sequences derived from a particular amino acid sequence may be variants of that particular sequence or a fragment thereof. For example, it will be understood by one of ordinary skill in the art that the epitopes suitable for use herein may be altered such that they vary in sequence from the naturally occurring or native sequences from which they were derived, while retaining the desirable activity of the native sequences.

RNA encoding polypeptides comprising one or more epitopes as described herein can be used to deliver epitopes derived from tumor-associated antigens encoded by excessively upregulated RNA transcripts to a patient. Dendritic cells (DCs) residing in the spleen represent antigen-presenting cells of particular interest for RNA expression of epitopes.

In one embodiment, RNA is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

In one embodiment, the RNA may have modified ribonucleotides. Examples of modified ribonucleotides include, without limitation, 5-methylcytidine, pseudouridine ($\psi$), N1-methyl-pseudouridine ($m^1\psi$) or 5-methyl-uridine ($m^5U$).

In some embodiments, the RNA according to the present disclosure comprises a 5'-cap. In one embodiment, the RNA of the present disclosure does not have uncapped 5'-triphosphates. In one embodiment, the RNA may be modified by a 5'-cap analog. The term "5'-cap" refers to a structure found on the 5'-end of an mRNA molecule and generally consists of a guanosine nucleotide connected to the mRNA via a 5' to 5' triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand, or may be attached to RNA post-transcriptionally using capping enzymes.

In some embodiments, RNA according to the present disclosure comprises a 5'-UTR and/or a 3'-UTR. The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a protein-encoding region. A 5'-UTR is downstream of the 5'-cap (if present), e.g. directly adjacent to the 5'-cap. A 3'-UTR, if present, is located at the 3' end, downstream of the termination codon of a protein-encoding region, but the term "3'-UTR" does preferably not include the poly(A) tail. Thus, the 3'-UTR is upstream of the poly(A) sequence (if present), e.g. directly adjacent to the poly(A) sequence.

In some embodiments, the RNA according to the present disclosure comprises a 3'-poly(A) sequence. The term "poly (A) sequence" relates to a sequence of adenyl (A) residues which typically is located at the 3'-end of a RNA molecule. According to the disclosure, in one embodiment, a poly(A) sequence comprises at least about 20, at least about 40, at least about 80, or at least about 100, and up to about 500, up to about 400, up to about 300, up to about 200, or up to about 150 A nucleotides, and in particular about 120 A nucleotides.

In the context of the present disclosure, the term "transcription" relates to a process, wherein the genetic code in a DNA sequence is transcribed into RNA. Subsequently, the RNA may be translated into peptide or protein.

With respect to RNA, the term "expression" or "translation" relates to the process in the ribosomes of a cell by which a strand of mRNA directs the assembly of a sequence of amino acids to make a peptide or protein.

RNA-Containing Particles

The RNA to be administered may be present within particles comprising RNA and one or more components which associate with RNA to form RNA particles. The RNA particles may comprise RNA in complexed and/or encapsulated form. The particles described herein preferably are not viral particles, in particular infectious viral particles, i.e., they are not able to virally infect cells. The RNA-containing particles may be, for example, in the form of proteinaceous particles or in the form of lipid-containing particles. Suitable proteins or lipids are included by the term "particle forming components" or "particle forming agents". The term "particle forming components" or "particle forming agents" relates to any components which associate with RNA to form RNA particles.

In the context of the present disclosure, the term "particle" relates to a structured entity formed by molecules or molecule complexes. In one embodiment, the term "particle" relates to a micro- or nano-sized structure, such as a micro- or nano-sized compact structure.

In the context of the present disclosure, the term "RNA particle" relates to a particle that contains RNA. Electrostatic interactions between positively charged molecules such as polymers and lipids and negatively charged RNA results in complexation and spontaneous formation of RNA particles. In one embodiment, a RNA particle is a nanoparticle.

As used in the present disclosure, "nanoparticle" in one embodiment refers to a particle having an average diameter suitable for intravenous administration.

Lipids, polymers, or amphipiles are typical constituents of RNA particle formulations.

Proteinaceous particles and lipid-containing particles have been described previously to be suitable for delivery of RNA in particulate form (e.g. Kaczmarek, J. C. et al., 2017, Genome Medicine 9, 60). For non-viral RNA delivery vehicles, nanoparticle encapsulation of RNA physically protects RNA from degradation and, depending on the specific chemistry, can aid in cellular uptake and endosomal escape. Given their high degree of chemical flexibility, polymers are commonly used materials for nanoparticle-based delivery. Typically, cationic polymers are used to electrostatically condense the negatively charged RNA into nanoparticles. These positively charged groups often consist of amines that become protonated at physiological pH (pKa ~7.4), thought to lead to an ion imbalance that results in endosomal rupture. Polymers such as poly-L-lysine, polyamidoamine, protamine and polyethyleneimine, as well as naturally occurring polymers such as chitosan have all been applied to RNA delivery. In addition, some investigators have synthesized polymers specifically for nucleic acid delivery. Poly(β-amino esters), in particular, have gained widespread use in nucleic acid delivery owing to their ease of synthesis and biodegradability.

A "polymer," as used herein, is given its ordinary meaning, i.e., a molecular structure comprising one or more repeat units (monomers), connected by covalent bonds. The repeat units can all be identical, or in some cases, there can be more than one type of repeat unit present within the polymer. In some cases, the polymer is biologically derived, i.e., a biopolymer such as a protein. In some cases, additional moieties can also be present in the polymer, for example targeting moieties such as those described herein.

If more than one type of repeat unit is present within the polymer, then the polymer is said to be a "copolymer." It is to be understood that in any embodiment employing a polymer, the polymer being employed can be a copolymer in some cases. The repeat units forming the copolymer can be arranged in any fashion. For example, the repeat units can be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers can have two (a diblock copolymer), three (a triblock copolymer), or more numbers of distinct blocks.

In certain embodiments, the polymer is biocompatible. Biocompatible polymers are polymers that typically do not result in significant cell death at moderate concentrations. In certain embodiments, the biocompatible polymer is biodegradable, i.e., the polymer is able to degrade, chemically and/or biologically, within a physiological environment, such as within the body. In certain embodiments, the polymer may be protamine or polyethyleneimine.

RNA may be delivered to spleen by so-called lipoplex formulations, in which the RNA is bound to liposomes comprising a cationic lipid and optionally an additional or helper lipid to form injectable nanoparticle formulations. The liposomes may be obtained by injecting a solution of the lipids in ethanol into water or a suitable aqueous phase. RNA lipoplex particles may be prepared by mixing the liposomes with RNA. Spleen targeting RNA lipoplex particles are described in WO 2013/143683, herein incorporated by reference. It has been found that RNA lipoplex particles having a net negative charge may be used to preferentially target spleen tissue or spleen cells such as antigen-presenting cells, in particular dendritic cells. Accordingly, following administration of the RNA lipoplex particles, RNA accumulation and/or RNA expression in the spleen occurs. Thus, RNA lipoplex particles of the disclosure may be used for expressing RNA in the spleen. In an embodiment, after administration of the RNA lipoplex particles, no or essentially no RNA accumulation and/or RNA expression in the lung and/or liver occurs. In one embodiment, after administration of the RNA lipoplex particles, RNA accumulation and/or RNA expression in antigen presenting cells, such as professional antigen presenting cells in the spleen occurs. Thus, RNA lipoplex particles of the disclosure may be used for expressing RNA in such antigen presenting cells. In one embodiment, the antigen presenting cells are dendritic cells and/or macrophages.

In the context of the present disclosure, the term "RNA lipoplex particle" relates to a particle that contains lipid, in particular cationic lipid, and RNA. Electrostatic interactions between positively charged liposomes and negatively charged RNA results in complexation and spontaneous formation of RNA lipoplex particles. Positively charged liposomes may be generally synthesized using a cationic lipid, such as DOTMA, and additional lipids, such as DOPE. In one embodiment, a RNA lipoplex particle is a nanoparticle.

As used herein, a "cationic lipid" refers to a lipid having a net positive charge. Cationic lipids bind negatively charged RNA by electrostatic interaction to the lipid matrix. Generally, cationic lipids possess a lipophilic moiety, such as a sterol, an acyl or diacyl chain, and the head group of the lipid typically carries the positive charge. Examples of cationic lipids include, but are not limited to 1,2-di-O-octadecenyl-3-trimethylammonium propane (DOTMA), dimethyldioctadecylammonium (DDAB); 1,2-dioleoyl-3-trimethylammonium propane (DOTAP); 1,2-dioleoyl-3-di-methylammonium-propane (DODAP); 1,2-diacyloxy-3-di-methylammonium propanes; 1,2-dialkyloxy-3-dimethylammonium propanes; dioctadecyldimethyl ammonium chloride (DODAC), 2,3-di(tetradecoxy)propyl-(2-hydroxyethyl)-dimethylazanium (DMRIE), 1,2-dimyris-toyl-sn-glycero-3-ethylphosphocholine (DMEPC), 1,2-dimyristoyl-3-trimethylammonium propane (DMTAP), 1,2-dioleyloxypropyl-3-dimethyl-hydroxyethyl ammonium bromide (DORIE), and 2,3-dioleoyloxy-N-[2(spermine car-boxamide)ethyl]-N,N-dimethyl-1-propanamium trifluoroac-etate (DOSPA). Preferred are DOTMA, DOTAP, DODAC, and DOSPA. In specific embodiments, the cationic lipid is DOTMA and/or DOTAP.

An additional lipid may be incorporated to adjust the overall positive to negative charge ratio and physical stabil-ity of the RNA lipoplex particles. In certain embodiments, the additional lipid is a neutral lipid. As used herein, a "neutral lipid" refers to a lipid having a net charge of zero. Examples of neutral lipids include, but are not limited to, 1,2-di-(9Z-octadecenoyl)-sn-glycero-3-phosphoetha-nolamine (DOPE), 1,2-dioleoyl-sn-glycero-3-phosphocho-line (DOPC), diacylphosphatidyl choline, diacylphosphati-dyl ethanol amine, ceramide, sphingoemyelin, cephalin, cholesterol, and cerebroside. In specific embodiments, the additional lipid is DOPE, cholesterol and/or DOPC.

In certain embodiments, the RNA lipoplex particles include both a cationic lipid and an additional lipid. In an exemplary embodiment, the cationic lipid is DOTMA and the additional lipid is DOPE.

In some embodiments, the molar ratio of the at least one cationic lipid to the at least one additional lipid is from about 10:0 to about 1:9, about 4:1 to about 1:2, or about 3:1 to about 1:1. In specific embodiments, the molar ratio may be about 3:1, about 2.75:1, about 2.5:1, about 2.25:1, about 2:1, about 1.75:1, about 1.5:1, about 1.25:1, or about 1:1. In an exemplary embodiment, the molar ratio of the at least one cationic lipid to the at least one additional lipid is about 2:1.

RNA lipoplex particles described herein have an average diameter that in one embodiment ranges from about 200 nm to about 1000 nm, from about 200 nm to about 800 nm, from about 250 to about 700 nm, from about 400 to about 600 nm, from about 300 nm to about 500 nm, or from about 350 nm to about 400 nm. In specific embodiments, the RNA lipoplex particles have an average diameter of about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 700 nm, about 725 nm, about 750 nm, about 775 nm, about 800 nm, about 825 nm, about 850 nm, about 875 nm, about 900 nm, about 925 nm, about 950 nm, about 975 nm, or about 1000 nm. In an embodi-ment, the RNA lipoplex particles have an average diameter that ranges from about 250 nm to about 700 nm. In another embodiment, the RNA lipoplex particles have an average diameter that ranges from about 300 nm to about 500 nm. In an exemplary embodiment, the RNA lipoplex particles have an average diameter of about 400 nm.

The term "average diameter" refers to the mean hydro-dynamic diameter of particles as measured by dynamic light scattering (DLS) with data analysis using the so-called cumulant algorithm, which provides as results the so-called $Z_{average}$ with the dimension of a length, and the polydisper-sity index (PI), which is dimensionless (Koppel, D., J. Chem. Phys. 57, 1972, pp 4814-4820, ISO 13321). Here "average diameter", "diameter" or "size" for particles is used synonymously with this value of the $Z_{average}$.

The term "polydispersity index" is used herein as a measure of the size distribution of an ensemble of particles, e.g., nanoparticles. The polydispersity index is calculated based on dynamic light scattering measurements by the so-called cumulant analysis.

The term "extruding" or "extrusion" refers to the creation of particles having a fixed, cross-sectional profile. In par-ticular, it refers to the downsizing of a particle, whereby the particle is forced through filters with defined pores.

The electric charge of the RNA-lipid particles of the present disclosure is the sum of the electric charges present in the at least one cationic lipid and the electric charges present in the RNA. The charge ratio is the ratio of the positive charges present in the at least one cationic lipid to the negative charges present in the RNA. The charge ratio of the positive charges present in the at least one cationic lipid to the negative charges present in the RNA is calculated by the following equation: charge ratio=[(cationic lipid con-centration (mol))*(the total number of positive charges in the cationic lipid)]/[(RNA concentration (mol))*(the total number of negative charges in RNA)].

The spleen targeting RNA lipoplex particles described herein at physiological pH preferably have a net negative charge such as a charge ratio of positive charges to negative charges from about 1.9:2 to about 1:2. In specific embodi-ments, the charge ratio of positive charges to negative charges in the RNA lipoplex particles at physiological pH is about 1.9:2.0, about 1.8:2.0, about 1.7:2.0, about 1.6:2.0, about 1.5:2.0, about 1.4:2.0, about 1.3:2.0, about 1.2:2.0, about 1.1:2.0, or about 1:2.0.

"Physiological pH" as used herein refers to a pH of about 7.5.

PHARMACEUTICAL COMPOSITIONS

The agents described herein are useful as or for preparing pharmaceutical compositions or medicaments, in particular vaccines for therapeutic or prophylactic treatments.

The term "pharmaceutical composition" relates to a for-mulation comprising a therapeutically effective agent, pref-erably together with pharmaceutically acceptable carriers, diluents and/or excipients. Said pharmaceutical composition is useful for treating, preventing, or reducing the severity of a disease or disorder by administration of said pharmaceu-tical composition to a subject. A pharmaceutical composi-tion is also known in the art as a pharmaceutical formulation.

In the context of the present disclosure, the pharmaceu-tical composition may comprise RNA, RNA particles and/or further agents as described herein.

According to the invention, the term "vaccine" relates to a pharmaceutical preparation (pharmaceutical composition) or product that upon administration induces an immune response, in particular a cellular immune response, which recognizes and attacks a pathogen or a diseased cell such as a cancer cell. A vaccine may be used for the prevention or treatment of a disease. The term "individualized cancer vaccine" concerns a particular cancer patient and means that a cancer vaccine is adapted to the needs or special circum-stances of an individual cancer patient.

The pharmaceutical compositions of the present disclo-sure preferably comprise one or more adjuvants or may be administered with one or more adjuvants. The term "adjuvant" relates to a compound which prolongs, enhances or accelerates an immune response. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples of adjuvants include, without limitation, LPS, GP96, CpG oligodeoxynucleotides, growth factors, and cyctokines, such as monokines, lymphokines, interleukins, chemokines. The chemokines may be IL1, IL2, IL3, IL4, IL5, IL6, IL7, IL8, IL9, IL10, IL12, IFNα, IFNγ, GM-CSF, LT-a. Further known adjuvants are aluminium hydroxide, Freund's adjuvant or oil such as Montanide® ISA51. Other suitable adjuvants for use in the present disclosure include lipopeptides, such as Pam3Cys.

The pharmaceutical compositions according to the present disclosure are generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The pharmaceutical compositions of the present disclosure may contain salts, buffers, preservatives, and optionally other therapeutic agents. In one embodiment, the pharmaceutical compositions of the present disclosure comprise one or more pharmaceutically acceptable carriers, diluents and/ or excipients.

Suitable preservatives for use in the pharmaceutical compositions of the present disclosure include, without limitation, benzalkonium chloride, chlorobutanol, paraben and thimerosal.

The term "excipient" as used herein refers to a substance which may be present in a pharmaceutical composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants.

The term "diluent" relates a diluting and/or thinning agent. Moreover, the term "diluent" includes any one or more of fluid, liquid or solid suspension and/or mixing media. Examples of suitable diluents include ethanol, glycerol and water.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carrier include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In one embodiment, the pharmaceutical composition of the present disclosure includes isotonic saline.

Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

Routes of Administration of Pharmaceutical Compositions

In one embodiment, pharmaceutical compositions described herein may be administered intravenously, intraarterially, subcutaneously, intradermally or intramuscularly. In certain embodiments, the pharmaceutical composition is formulated for local administration or systemic administration. Systemic administration may include enteral administration, which involves absorption through the gastrointestinal tract, or parenteral administration. As used herein, "parenteral administration" refers to the administration in any manner other than through the gastrointestinal tract, such as by intravenous injection. In a preferred embodiment, the pharmaceutical compositions is formulated for systemic administration. In another preferred embodiment, the systemic administration is by intravenous administration.

In one embodiment, after administration of the pharmaceutical compositions described herein, at least a portion of the active agent such polypeptide comprising one or more epitopes or nucleic acid, in particular RNA encoding said polypeptide, optionally in the form of RNA particles, is delivered to a target cell. In one embodiment, at least a portion of the RNA is delivered to the cytosol of the target cell. In one embodiment, the RNA is translated by the target cell to produce the polypeptide. In one embodiment, the target cell is a spleen cell. In one embodiment, the target cell is an antigen presenting cell such as a professional antigen presenting cell in the spleen. In one embodiment, the target cell is a dendritic cell in the spleen. Thus, RNA particles described herein may be used for delivering RNA to such target cell. Accordingly, the present disclosure also relates to a method for delivering RNA to a target cell in a subject comprising the administration of the RNA particles described herein to the subject. In one embodiment, the RNA is delivered to the cytosol of the target cell. In one embodiment, the RNA is RNA encoding a polypeptide comprising one or more epitopes and the RNA is translated by the target cell to produce the polypeptide.

In one embodiment, the disclosure involves targeting the lymphatic system, in particular secondary lymphoid organs, more specifically spleen.

The "lymphatic system" is part of the circulatory system and an important part of the immune system, comprising a network of lymphatic vessels that carry lymph. The lymphatic system consists of lymphatic organs, a conducting network of lymphatic vessels, and the circulating lymph. The primary or central lymphoid organs generate lymphocytes from immature progenitor cells. The thymus and the bone marrow constitute the primary lymphoid organs. Secondary or peripheral lymphoid organs, which include lymph nodes and the spleen, maintain mature naive lymphocytes and initiate an adaptive immune response.

Use of Pharmaceutical Compositions

Vaccines described herein may be used in the therapeutic or prophylactic treatment of a cancer disease.

In one embodiment, the present disclosure relates to a method for inducing an immune response in a subject comprising administering to the subject a vaccine as described herein. In an exemplary embodiment, the immune response is against cancer.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

In the present context, the term "treatment", "treating" or "therapeutic intervention" relates to the management and care of a subject for the purpose of combating a condition such as a disease or disorder. The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to a human or another mammal (e.g. mouse, rat, rabbit, dog, cat, cattle, swine, sheep, horse or primate) that can be afflicted with or is susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In embodiments of the present disclosure, the "individual" or "subject" is a "patient".

The term "patient" means an individual or subject for treatment, in particular a diseased individual or subject.

In one embodiment of the disclosure, the aim is to provide an immune response against diseased cells expressing an antigen such as cancer cells expressing a tumor antigen, and to treat a disease such as a cancer disease involving cells expressing an antigen such as a tumor antigen.

A vaccine as described herein that comprises a polypeptide comprising one or more epitopes encoded by one or more excessively upregulated RNA transcripts, or a nucleic acid encoding said polypeptide may be administered to a subject to elicit an immune response against the one or more epitopes in the subject which may be therapeutic or partially or fully protective. A person skilled in the art will know that one of the principles of immunotherapy and vaccination is based on the fact that an immunoprotective reaction to a disease is produced by immunizing a subject with an antigen or an epitope, which is immunologically relevant with respect to the disease to be treated. Accordingly, pharmaceutical compositions described herein are applicable for inducing or enhancing an immune response. Pharmaceutical compositions described herein are thus useful in a prophylactic and/or therapeutic treatment of a disease involving an antigen or epitope.

As used herein, "immune response" refers to an integrated bodily response to an antigen or a cell expressing an antigen and refers to a cellular immune response and/or a humoral immune response. A cellular immune response includes, without limitation, a cellular response directed to cells expressing an antigen and being characterized by presentation of an antigen with class I or class II MHC molecule. The cellular response relates to T lymphocytes, which may be classified as helper T cells (also termed CD4+ T cells) that play a central role by regulating the immune response or killer cells (also termed cytotoxic T cells, CD8+ T cells, or CTLs) that induce apoptosis in infected cells or cancer cells. In one embodiment, administering a pharmaceutical composition of the present disclosure involves stimulation of an anti-tumor CD8+ T cell response against cancer cells expressing one or more tumor antigens. In as specific embodiment, the tumor antigens are presented with class I MHC molecule.

The present disclosure contemplates an immune response that may be protective, preventive, prophylactic and/or therapeutic. As used herein, "induces [or inducing] an immune response" may indicate that no immune response against a particular antigen was present before induction or it may indicate that there was a basal level of immune response against a particular antigen before induction, which was enhanced after induction. Therefore, "induces [or inducing] an immune response" includes "enhances [or enhancing] an immune response".

The term "immunotherapy" relates to the treatment of a disease or condition by inducing, or enhancing an immune response. The term "immunotherapy" includes antigen immunization or antigen vaccination.

The terms "immunization" or "vaccination" describe the process of administering an antigen to an individual with the purpose of inducing an immune response, for example, for therapeutic or prophylactic reasons.

In one embodiment, the present disclosure envisions embodiments wherein RNA particles as described herein targeting spleen tissue are administered. The RNA encodes a polypeptide comprising one or more epitopes encoded by one or more excessively upregulated RNA transcripts as described, for example, herein. The RNA is taken up by antigen-presenting cells in the spleen such as dendritic cells to express the polypeptide. Following optional processing and presentation by the antigen-presenting cells an immune response may be generated against the one or more epitopes resulting in a prophylactic and/or therapeutic treatment of cancer. In one embodiment, the immune response induced by the RNA particles described herein comprises presentation of one or more epitopes by antigen presenting cells, such as dendritic cells and/or macrophages, and activation of cytotoxic T cells due to this presentation. For example, polypeptides encoded by the RNAs or procession products thereof may be presented by major histocompatibility complex (MHC) proteins expressed on antigen presenting cells. The MHC peptide complex can then be recognized by immune cells such as T cells or B cells leading to their activation.

Thus, in one embodiment the RNA in the RNA particles described herein, following administration, is delivered to the spleen and/or is expressed in the spleen. In one embodiment, the RNA particles are delivered to the spleen for activating splenic antigen presenting cells. Thus, in one embodiment, after administration of the RNA particles RNA delivery and/or RNA expression in antigen presenting cells occurs. Antigen presenting cells may be professional antigen presenting cells or non-professional antigen presenting cells. The professional antigen presenting cells may be dendritic cells and/or macrophages, even more preferably splenic dendritic cells and/or splenic macrophages.

Accordingly, the present disclosure relates to RNA particles or a pharmaceutical composition comprising RNA particles as described herein for inducing or enhancing an immune response against cancer.

In a further embodiment, the present disclosure relates to RNA particles or a pharmaceutical composition comprising RNA particles as described herein for use in a prophylactic and/or therapeutic treatment of a cancer disease.

In a further embodiment, the present disclosure relates to a method for delivering one or more epitopes to antigen presenting cells, such as professional antigen presenting cells, in the spleen, or expressing one or more epitopes in antigen presenting cells, such as professional antigen presenting cells, in the spleen comprising administering to a subject RNA particles or a pharmaceutical composition comprising RNA particles as described herein. The one or more epitopes are preferably encoded by the RNA in the RNA particles.

In one embodiment, systemically administering RNA particles or a pharmaceutical composition comprising RNA particles as described herein results in targeting and/or accumulation of the RNA particles or RNA in the spleen and not in the lung and/or liver. In one embodiment, RNA particles release RNA in the spleen and/or enter cells in the spleen. In one embodiment, systemically administering RNA particles or a pharmaceutical composition comprising RNA particles as described herein delivers the RNA to antigen presenting cells in the spleen. In a specific embodiment, the antigen presenting cells in the spleen are dendritic cells or macrophages.

In a further embodiment, the present disclosure relates to a method for inducing or enhancing an immune response against cancer in a subject comprising administering to the subject RNA particles or a pharmaceutical composition comprising RNA particles as described herein.

The term "macrophage" refers to a subgroup of phagocytic cells produced by the differentiation of monocytes. Macrophages which are activated by inflammation, immune cytokines or microbial products nonspecifically engulf and kill foreign pathogens within the macrophage by hydrolytic and oxidative attack resulting in degradation of the pathogen. Peptides from degraded proteins are displayed on the macrophage cell surface where they can be recognized by T cells, and they can directly interact with antibodies on the B cell surface, resulting in T and B cell activation and further stimulation of the immune response. Macrophages belong to the class of antigen presenting cells. In one embodiment, the macrophages are splenic macrophages.

The term "dendritic cell" (DC) refers to another subtype of phagocytic cells belonging to the class of antigen presenting cells. In one embodiment, dendritic cells are derived from hematopoietic bone marrow progenitor cells. These progenitor cells initially transform into immature dendritic cells. These immature cells are characterized by high phagocytic activity and low T cell activation potential. Immature dendritic cells constantly sample the surrounding environment for pathogens such as viruses and bacteria. Once they have come into contact with a presentable antigen, they become activated into mature dendritic cells and begin to migrate to the spleen or to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T cell activation such as CD80, CD86, and CD40 greatly enhancing their ability to activate T cells. They also upregulate CCR7, a chemotactic receptor that induces the dendritic cell to travel through the blood stream to the spleen or through the lymphatic system to a lymph node. Here they act as antigen-presenting cells and activate helper T cells and killer T cells as well as B cells by presenting them antigens, alongside non-antigen specific co-stimulatory signals. Thus, dendritic cells can actively induce a T cell- or B cell-related immune response. In one embodiment, the dendritic cells are splenic dendritic cells.

The term "antigen presenting cell" (APC) is a cell of a variety of cells capable of displaying, acquiring, and/or presenting at least one antigen or antigenic fragment on (or at) its cell surface. Antigen-presenting cells can be distinguished in professional antigen presenting cells and non-professional antigen presenting cells.

The term "professional antigen presenting cells" relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term "non-professional antigen presenting cells" relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, such as antigen presenting cells to specific T cells.

The term "disease involving an antigen" or "disease involving an epitope" refers to any disease which implicates an antigen or epitope, e.g. a disease which is characterized by the presence of an antigen or epitope. The disease involving an antigen or epitope can be a cancer disease or simply cancer. As mentioned above, the antigen may be a disease-associated antigen, such as a tumor-associated antigen.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the disclosure also comprises cancer metastases. Generally, the terms "tumor" and "cancer" are used interchangeably herein.

The term "circulating tumor cells" or "CTCs" relates to cells that have detached from a primary tumor or tumor metastases and circulate in the bloodstream. CTCs may constitute seeds for subsequent growth of additional tumors (metastasis) in different tissues. Circulating tumor cells are found in frequencies in the order of 1-10 CTC per mL of whole blood in patients with metastatic disease. Research methods have been developed to isolate CTC. Several research methods have been described in the art to isolate CTCs, e.g. techniques which use of the fact that epithelial cells commonly express the cell adhesion protein EpCAM, which is absent in normal blood cells. Immunomagnetic bead-based capture involves treating blood specimens with antibody to EpCAM that has been conjugated with magnetic particles, followed by separation of tagged cells in a magnetic field. Isolated cells are then stained with antibody to another epithelial marker, cytokeratin, as well as a common leukocyte marker CD45, so as to distinguish rare CTCs from contaminating white blood cells. This robust and semiautomated approach identifies CTCs with an average yield of approximately 1 CTC/mL and a purity of 0.1% (Allard et al., 2004: Clin Cancer Res 10, 6897-6904). A second method for isolating CTCs uses a microfluidic-based CTC capture device which involves flowing whole blood through a chamber embedded with 80,000 microposts that have been rendered functional by coating with antibody to EpCAM. CTCs are then stained with secondary antibodies against either cytokeratin or tissue specific markers, such as PSA in prostate cancer or HER2 in breast cancer and are visualized by automated scanning of microposts in multiple planes along three dimensional coordinates. CTC-chips are able to identifying cytokerating-positive circulating tumor cells in patients with a median yield of 50 cells/ml and purity ranging from 1-80% (Nagrath et al., 2007: Nature 450, 1235-1239). Another possibility for isolating CTCs is using the CellSearch™ Circulating Tumor Cell (CTC) Test from Veridex, LLC (Raritan, NJ) which captures, identifies, and counts CTCs in a tube of blood. The CellSearch™ system is a U.S. Food and Drug Administration (FDA) approved methodology for enumeration of CTC in whole blood which is based on a combination of immunomagnetic labeling and automated digital microscopy. There are other methods for isolating CTCs described in the literature all of which can be used in conjunction with the present invention.

Combination strategies in cancer treatment may be desirable due to a resulting synergistic effect, which may be considerably stronger than the impact of a monotherapeutic approach. In one embodiment, the pharmaceutical composition is administered with an immunotherapeutic agent. As used herein "immunotherapeutic agent" relates to any agent that may be involved in activating a specific immune response and/or immune effector function(s). The present disclosure contemplates the use of an antibody as an immunotherapeutic agent. Without wishing to be bound by theory, antibodies are capable of achieving a therapeutic effect against cancer cells through various mechanisms, including inducing apoptosis, block components of signal transduction pathways or inhibiting proliferation of tumor cells. In certain embodiments, the antibody is a monoclonal antibody. A monoclonal antibody may induce cell death via antibody-dependent cell mediated cytotoxicity (ADCC), or bind complement proteins, leading to direct cell toxicity, known as complement dependent cytotoxicity (CDC). Non-limiting examples of anti-cancer antibodies and potential antibody targets (in brackets) which may be used in combination with the present disclosure include: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Atezolizumab (PD-L1), Bavituximab (phosphatidylserine), Bectumomab (CD22), Belimumab (BAFF), Bevacizumab (VEGF-A), Bivatuzumab mertansine (CD44 v6), Blinatumomab (CD 19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNT0888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin αvβ3), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-β), Galiximab (CD80), Ganitumab (IGF-I), Gemtuzumab ozogamicin (CD33), Gevokizumab (IL-Iβ), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), Inotuzumab ozogamicin (CD22), Ipilimumab (CD 152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL-5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Namatumab (RON), Necitumumab (EGFR), Nimotuzumab (EGFR), Nivolumab (IgG4), Ofatumumab (CD20), Olaratumab (PDGF-R a), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzuma (HER2/neu), Pintumomab (adenocarcinoma antigen), Pritumumab (vimentin), Racotumomab (N-glycolylneuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL-6), Tabalumab (BAFF), Tacatuzumab tetraxetan (alpha-fetoprotein), Taplitumomab paptox (CD 19), Tenatumomab (tenascin C), Teprotumumab (CD221), Ticilimumab (CTLA-4), Tigatuzumab (TRAIL-R2), TNX-650 (IL-13), Tositumomab (CD20), Trastuzumab (HER2/neu), TRBS07 (GD2), Tremelimumab (CTLA-4), Tucotuzumab celmoleukin (EpCAM), Ublituximab (MS4A1), Urelumab (4-1 BB), Volociximab (integrin $\alpha 5\beta 1$), Votumumab (tumor antigen CTAA 16.88), Zalutumumab (EGFR), and Zanolimumab (CD4).

In one embodiment, the immunotherapeutic agent is a PD-1 axis binding antagonist. A PD-1 axis binding antagonist includes but is not limited to a PD-1 binding antagonist, a PD-L1 binding antagonist and a PD-L2 binding antagonist. Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific embodiment, PD-L1 binding partners are PD-1 and/or B7-1. In another embodiment, the PD-L2 binding antagonist is a molecule that inhibits the binding of PD-L2 to its binding partners. In a specific embodiment, the PD-L2 binding partner is PD-1. The PD-1 binding antagonist may be an antibody, an antigen binding fragment thereof, an immunoadhesin, a fusion protein, or oligopeptide. In some embodiments, the PD-1 binding antagonist is an anti-PD-1 antibody (e.g., a human antibody, a humanized antibody, or a chimeric antibody). Examples of an anti-PD-1 antibody include, without limitation, MDX-1106 (Nivolumab, OPDIVO), Merck 3475 (MK-3475, Pembrolizumab, KEYTRUDA), MEDI-0680 (AMP-514), PDR001, REGN2810, BGB-108, and BGB-A317.

In one embodiment, the PD-1 binding antagonist is an immunoadhesin that includes an extracellular or PD-1 binding portion of PD-L1 or PD-L2 fused to a constant region. In one embodiment, the PD-1 binding antagonist is AMP- 224 (also known as B7-DCIg, is a PD-L2-Fc), which is fusion soluble receptor described in WO2010/027827 and WO2011/066342.

In one embodiment, the PD-1 binding antagonist is an anti-PD-L1 antibody, including, without limitation, YW243.55.S70, MPDL3280A (Atezolizumab), MEDI4736 (Durvalumab), MDX-1105, and MSB0010718C (Avelumab).

In one embodiment, the immunotherapeutic agent is a PD-1 binding antagonist. In another embodiment, the PD-1 binding antagonist is an anti-PD-L1 antibody. In an exemplary embodiment, the anti-PD-L1 antibody is Atezolizumab.

Citation of documents and studies referenced herein is not intended as an admission that any of the foregoing is pertinent prior art. All statements as to the contents of these documents are based on the information available to the applicants and do not constitute any admission as to the correctness of the contents of these documents.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Example 1: Selection of Differentially Expressed Genes in the B16-F10 Melanoma Cell Line The mRNA-derived cDNA of the melanoma cell line B16-F10 was sequenced (Castle, J. C. et al. Cancer Res. 72, 1081-1091 (2012)). Gene expression abundance was estimated using the pseudoalignment software kallisto (Bray, N. L. et al. Nat. Biotech. 34, 525-527 (2016)) and reported as transcripts per million (TPM). The gene expression values were then compared to a reference gene expression database of selected normal tissues processed in the same manner. The reference database included samples from the Mouse ENCODE project (n=487) (Pervouchine, D. D. et al. Nat. Comm. 6, 5903 (2015)), from the Mouse Transcriptomic BodyMap (n=72) (Li, B. et al. Sci. Rep. 7(1):4200 (2017)), the murine samples from the Circadian Gene Expression Atlas (n=96) (Zhang, R. et al. PNAS 111(45):16219-24 (2014)), and samples from internally sequenced murine tissues (n=67). Samples were annotated with respect to the tissue source and the tissue class. Tissue classes include embryonic tissues (all samples annotated as 'embryonic'), reproductive tissues (vesicular gland, uterus, ovary, placenta, and testis), and normal tissues (all other). For each unique tissue, the median expression of all samples was calculated. B16-F10 targets were then pre-selected, if they exceeded the cutoff c calculated as $$c=10*M+1,$$

where M equals the 95-th percentile of all normal tissue medians. Finally, the potential target list was sorted by the fold change of expressed genes in B16-F10 compared to the sum of expression values in the normal tissues. Expression in reproductive organs as well as embryonic tissue was allowed (these so called cancer germline antigens are solely present in the tumor, in male germ cells, placenta or in early stages of embryonic development).

Figure 1A:
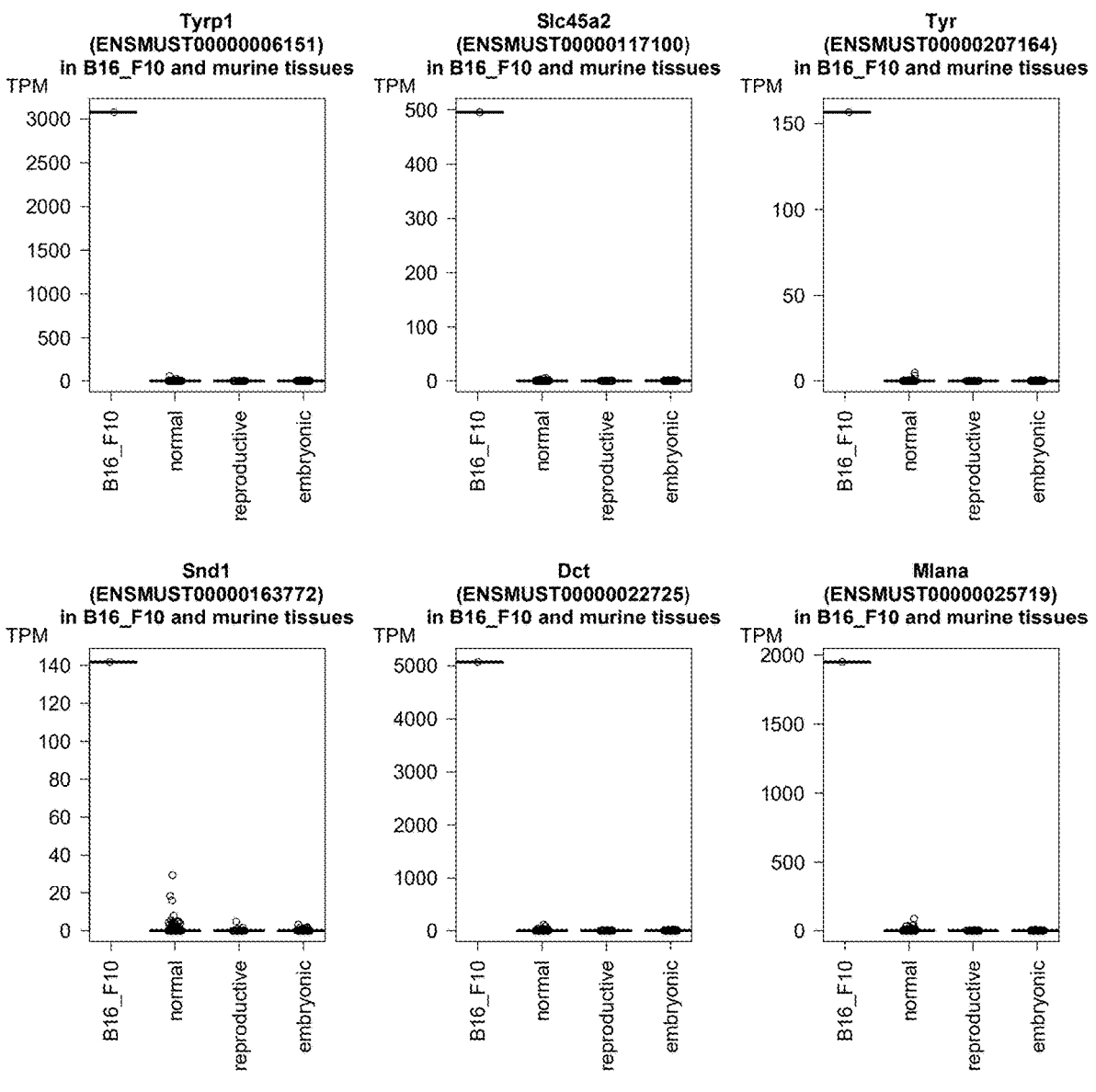
FIGS. 1A and 1B: Examples of differentially expressed genes in the B16-F10 melanoma cell line Expression values in transcripts per million (TPM) of selected genes in the melanoma cell line B16-F10 and murine tissues subdivided into three classes: normal tissues (n=46), reproductive tissues (n=5), and embryonic tissues (n=14). Tissue expression given as the median of all samples per tissue. Circles indicate single tissue medians. Boxplot center line indicates the median of all tissues, the box depicts the first and the third quartile, whiskers are 2.5-times quartile distance from the median.
Figure 1B:
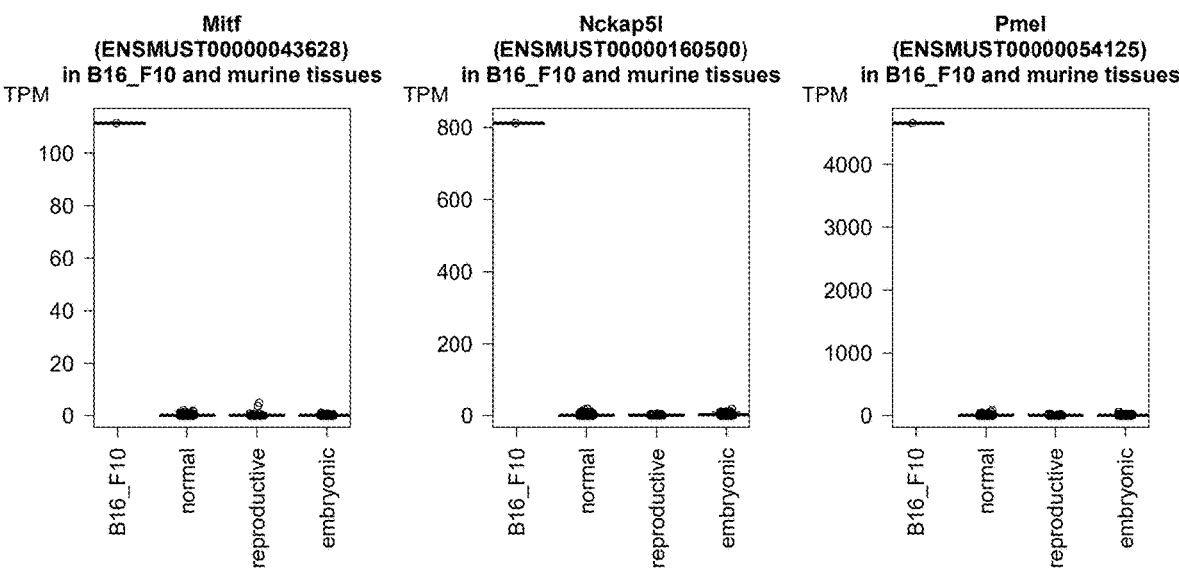
Figure 1B:
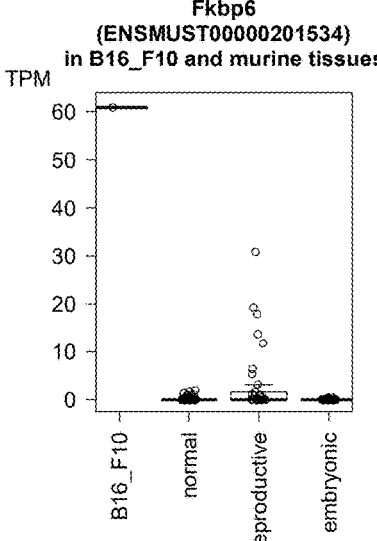

Among the top differentially expressed genes in the mouse B16-F10 melanoma cell line we found several well-known melanoma differentiation antigens (FIG. 1). For example, among the top 10 genes ranked by our algorithm we found the known immunogenic antigens tyrosinase-related protein 1 (Tyrp1, rank 1, Wang, R. et al. *J. Exp. Med.* 183, 1131-40 (1996)), solute carrier family 45, member 2 (Slc45a2, rank 2, Park, J. et al. Cancer Immunol. Res. 5, 618-629 (2017).), tyrosinase (Tyr, rank 3, Wölfel, T. et al. *Eur. J. Immunol.* 24, 759-64 (1994).), dopachrome tautomerase (Dct, rank 5, Wang, R. F. et al. *J. Exp. Med.* 184, 2207-16 (1996).), mlan-A (Mlana, rank 6, Kawakami, Y. et al. *J. Exp. Med.* 180, 347-52 (1994).) and premelanosome protein (Pmel, rank 9, Kawakami, Y. et al. *J. Immunol.* 154, 3961-8 (1995).). This impressively demonstrates the potency of our algorithm to enrich for relevant tumor antigens. Among the above mentioned targets, we selected Tyrp1, Tyr, Dct, Pmel and Fkbp6 for first proof of concept studies. Vaccination against all targets except for Tyr elicited strong T cell immune responses (Example 2-5).

Example 2: Immunogenicity Testing of a Tyrp1 RNA Vaccine

Figure 2:
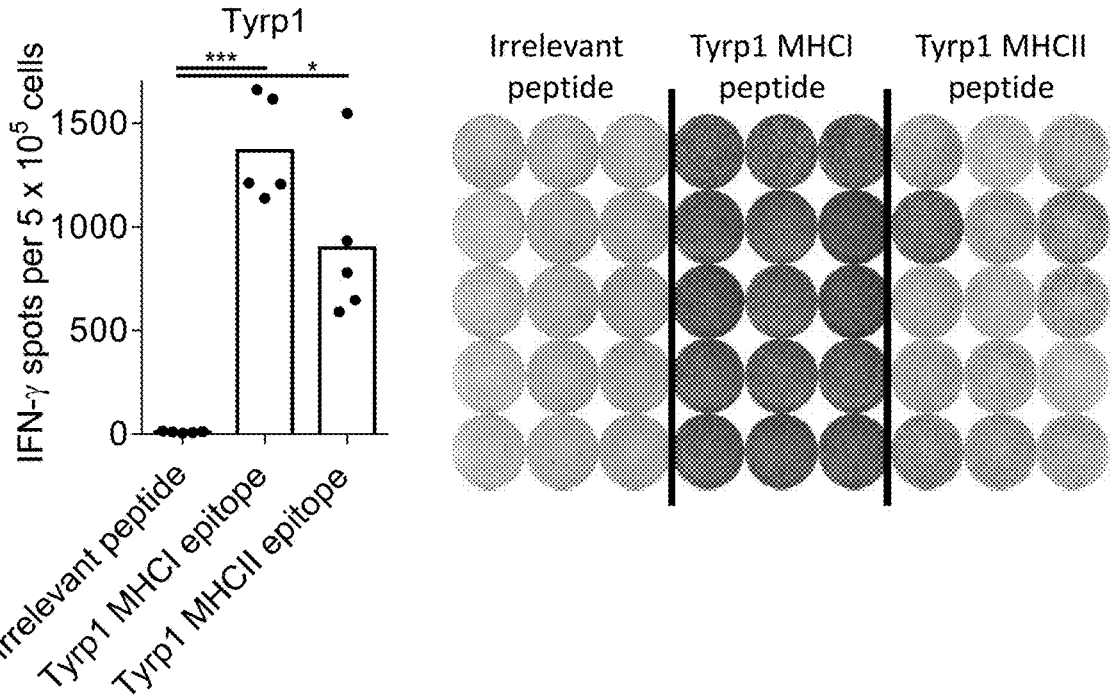
FIG. 2: Immunogenicity testing of a Tyrp1 RNA vaccine

C57BL/6 mice (n=5 per group) were immunized with 40 μg Tyrp1 antigen encoding RNA formulated as lipoplexes or 40 μg irrelevant RNA on days 0, 7 and 14 as described in Kranz, L. M. et al. *Nature* 534, 396-401 (2016). Five days after the last vaccination, splenocytes of mice were isolated and $5 \times 10^5$ cells tested by IFNγ ELISpot for recognition of two Tyrp1 peptides encoding a MHC I epitope (TAP-DNLGYA; SEQ ID NO:3, 2 μg/ml) and MHC II (CRPGWRGAACNQKI; SEQ ID NO:4, 2 μg/ml) epitope, respectively. Vaccination against Tyrp1 resulted in potent CD4$^+$ and CD8$^+$ T-cell responses (FIG. 2). Statistical significance was determined by One way ANOVA and Dunett's multiple comparison test using GraphPad Prism 6. n.s.: P>0.05, *P<0.05, P<0.01, *P<0.001.

Example 3: Immunogenicity Testing of a Dct RNA Vaccine

Similarly to Example 2, C57BL/6 mice (n=5 per group) were repetitively vaccinated with 20 μg Dct encoding RNA lipoplexes or NaCl as indicated in FIG. 3 (dotted lines). On days 5, 12, 19, 26 and 33 after the first vaccination CD8$^+$ T-cell responses against Dct (SVYDFFVW; SEQ ID NO:5) were measured in blood via MHC tetramer (MBL international) staining by flow cytometry (as described in Kranz, L. M. et al. *Nature* 534, 396-401 (2016)). Repetitive vaccination resulted in constant increase of antigen specific T-cells exceeding 4% of all peripheral CD8$^+$ T cells by day 33. Statistical significance was determined by Two way ANOVA and Sidak's multiple comparison test using GraphPad Prism 6. n.s.: P>0.05, *P<0.05, P<0.01, *P<0.001.

Example 4: Immunogenicity Testing of a Pmel RNA Vaccine

As in Example 2, C57BL/6 mice (n=8 per group) were repetitively vaccinated with 20 μg Pmel encoding RNA lipoplexes as shown in FIG. 4. 27 days after the first vaccination splenocytes of mice were probed against a Pmel peptide (EGSRNQDWL; SEQ ID NO:6, 2 μg/ml) or irrelevant peptide (VSV-NP, RGYVYQGL; SEQ ID NO:7, 2 μg/ml) by IFNγ ELISpot. Significant Pmel specific CD8$^+$ T-cell responses were detected as determined by paired two-tailed student T-test. n.s.: P>0.05, *P<0.05, P<0.01, *P<0.001.

Example 5: Immunogenicity Testing of a Fkbp6 RNA Vaccine

C57BL/6 mice (n=3 per group) were immunized with 20 μg Fkbp6 antigen encoding RNA formulated as lipoplexes on days 0, 7 and 14 as described in Example 2. Five days after the last vaccination, splenocytes of mice were isolated and 5×105 cells tested by IFNγ ELISpot for recognition of syngeneic bone-marrow-derived dendritic cells (BMDCs) electroporated with 10 μg Fkbp6 RNA or irrelevant RNA (Control). BMDCs were generated by culturing bone marrow derived cells in the presence of GM-CSF (Lutz, M. B. et al. J. Immunol. Methods 223, 77-92 (1999)). Vaccination against Fkbp6 resulted in a potent T-cell response (FIG. 5).

Example 6: Tumor Control after Therapeutic Tyrp1 Vaccination

To test whether the selected vaccine targets are therapeutically meaningful we inoculated C57BL/6 mice (n=11-12 per group) intravenously (i.v.) with $3 \times 10^5$ B16-F10 tumor cells. Four days after tumor cell injection, RNA lipoplex vaccination with Tyrp1 or irrelevant control (backbone without antigen) RNA (40 μg) was started as shown in FIG. 6. 26 days after the start of the experiment lungs of mice were resected and tumor nodules counted. All control RNA treated mice demonstrated countless tumor nodules (exceeding a minimum of 500 nodules per mouse) and the majority of mice had to be sacrificed before day 26 due to sickness. In stark contrast, Tyrp1 vaccinated mice survived until day 26 with the majority of mice showing no macroscopic signs of tumor. Significance was determined using an unpaired, two-tailed Mann-Whitney test (comparison of tumor nodules) and log-rank test (survival). n.s.: P>0.05, *P<0.05, P<0.01, *P<0.001.

Example 7: Tumor Control after Therapeutic Tyrp1 or Dct Vaccination

Using a similar experimental set up that allowed the definition of a tumor growth kinetic we confirmed the therapeutic potential of Tyrp1 vaccination and additionally tested the effect of Dct RNA treatment on tumor growth. $3 \times 10^5$ luciferase transgenic B16-F10 tumor cells (B16-F10-LUC) were injected i.v. into naïve C57BL/6 mice (n=12 per group) and vaccinated with 40 μg RNA lipoplexes as indicated in FIG. 7. Tumor growth determined by luciferase bioluminescence was measured on days 4, 7, 12, 17, 19 and 25 by IVIS bioluminescence imaging system (as described in Kranz, L. M. et al. *Nature* 534, 396-401 (2016)). A significantly lower bioluminescence signal compared to untreated or irrelevant RNA treated groups indicating reduced tumor burden was reached by Tyrp1 and Dct vaccination. This was confirmed by independent read outs comparing tumor nodule count or lung weight 25 days after tumor inoculation. Significance was determined using a Two way ANOVA and Dunnett's multiple comparison test (comparison of Luciferase bioluminescence over time) or a Kruskal-Wallis test followed by Dunn's test (comparison of tumor nodules or lung weight). n.s.: P>0.05, *P<0.05, P<0.01, *P<0.001.

Example 8: Identification of Multiple so Far Undescribed Differentially Expressed Genes in the Tumor Models CT26, MC38, TRAMP-C2 and 4T1

Examples 1-7 demonstrated that it is possible to identify differentially expressed genes in an individual tumor by comparison of RNA sequencing based gene expression to a gene expression database of healthy tissues. Among the top ranked B16-F10 genes, several known tumor antigens were found. We demonstrated that RNA lipoplex vaccination against four out of five tested candidates resulted in strong T-cell responses. For two of these candidates, we showed that therapeutic vaccination resulted in strong anti-tumor immune responses leading to complete tumor rejection.

We subsequently extended our tumor models to test whether it is feasible to identify differentially expressed genes in other tumor types as well. Hence, we sequenced the mouse colon tumor cell lines CT26 and MC38, the prostate cancer cell line TRAMP-C2 as well as the breast cancer cell line 4T1 (sequencing described in Kreiter, S. et al. *Nature* 520, 692-696 (2015).) and compared RNA gene expression of the cell line to our healthy tissue database. Multiple differentially expressed genes were identified in each cell line, of which a selection is depicted in FIG. 8. Immunogenicity studies of selected candidates are described in Example 9.

Example 9: Immunogenicity Testing of Selected Targets in CT26, MC38 and TRAMP-C2

BALB/c (n=3, CT26) or C57BL/6 mice (n=3 per group, MC38 and TRAPM-C2) were immunized with 20 µg antigen encoding RNA formulated as lipoplexes on days 0, 7 and 14 as described in Example 2. For most groups, two antigens per mouse were injected. Five days after the last vaccination, splenocytes of mice were isolated and $5 \times 10^5$ cells tested by IFNγ ELISpot for recognition of syngeneic bone-marrow-derived dendritic cells (BMDCs) electroporated with 10 µg antigen RNA or irrelevant RNA (Control). BMDCs were generated by culturing bone marrow derived cells in the presence of GM-CSF (Lutz, M. B. et al. J. Immunol. Methods 223, 77-92 (1999)). Immune responses were identified against the CT26 derived targets Rhox5 and Ndst4 (FIG. 9), the MC38 derived targets GM14819, Rhox2h, Gm15091, Gm15097, Dppa4, GM773, Prl2c2, Fmr1nb and Luzp4 (FIG. 10) as well as against the TRAPM-C2 target Amot12 (FIG. 11).

Example 10: Selection of Differentially Expressed Genes for Personalized Cancer Immunotherapy in Humans For the determination of potential targets in an individual patient, mRNA-derived cDNA of the tumor would be sequenced and gene expression abundance estimated. The gene expression values would then be compared to a reference gene expression database of selected normal tissues processed in the same manner. The reference database might include the RNA-Seq data from normal samples from the Genotype-Tissue Expression (GTEx) database, the Human Protein Atlas (HPA), normal tissues from The Cancer Genome Atlas (TCGA), the Blueprint Epigenome database, and other cohorts. Selection of highly expressed antigens would be performed according to Example 1. After selection, potential targets would be validated before final selection for a vaccination therapy.

---

The invention claimed is:

1. A method for producing an individualized therapeutic cancer vaccine comprising the steps:

(a) identifying one or more RNA transcripts present in a tumor specimen of a human cancer patient, wherein each of the one or more RNA transcripts encodes an amino acid sequence and wherein each of the one or more RNA transcripts is present in the tumor specimen in a copy number that exceeds a pre-determined expression threshold; and (b) providing a vaccine comprising a polypeptide, wherein the polypeptide comprises one or more epitopes encoded by the one or more identified RNA transcripts, or a nucleic acid encoding said polypeptide, wherein the step of identifying one or more RNA transcripts comprises determining the copy number of RNA transcripts present in the tumor specimen of the human cancer patient and comparing the copy number of each of the RNA transcripts to a respective pre-determined expression threshold, wherein said pre-determined expression threshold is obtained by annotating reference samples to 10 or more non-tumor tissues, calculating the median RNA expression of all samples for each unique tissue and calculating expression threshold c as $$c = 10 * M + 1,$$

where M equals the $95^{th}$ percentile of all tissue RNA medians.

2. The method according to claim 1, wherein the step of identifying one or more RNA transcripts comprises single cell sequencing of one or more cancer cells.

3. The method according to claim 2, wherein the cancer cells are circulating tumor cells.

4. The method according to claim 1, wherein the step of identifying one or more RNA transcripts involves using next generation sequencing (NGS).

5. The method according to claim 1, wherein the step of identifying one or more RNA transcripts comprises sequencing RNA of the tumor specimen and/or a DNA library obtained from the RNA of the tumor specimen.

6. The method according to claim 1, wherein the epitopes are flanked N-terminally and/or C-terminally by amino acid sequences comprising 3 or more, 5 or more, or 10 or more amino acids also flanking said epitopes in the naturally occurring protein so as to form a vaccine sequence, and wherein the vaccine sequence is about 30 amino acids long.

7. The method according to claim 1, wherein the vaccine comprises a fusion polypeptide comprising at least two epitopes and/or vaccine sequences comprising epitopes.

8. The method according to claim 1, wherein the vaccine comprises a fusion polypeptide comprising at least two epitopes and/or vaccine sequences comprising epitopes and wherein the epitopes and/or vaccine sequences are spaced by linkers.

* * * * *

SEQUENCE LISTING

```
<160> NUMBER OF SEQ ID NOS: 7

<210> SEQ ID NO 1
<211> LENGTH: 15
<212> TYPE: PRT
<213> ORGANISM: Artificial Sequence
<220> FEATURE:
<223> OTHER INFORMATION: Linker sequence
<220> FEATURE:
<221> NAME/KEY: REPEAT
<222> LOCATION: (1)..(3)
<223> OTHER INFORMATION: Portion of sequence repeated a times, wherein a
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: MISC_FEATURE
<222> LOCATION: (1)..(15)
<223> OTHER INFORMATION: a + b + c + d + e are different from 0 and
      preferably are 2 or more, 3 or more, 4 or more or 5 or more
<220> FEATURE:
<221> NAME/KEY: REPEAT
<222> LOCATION: (4)..(6)
<223> OTHER INFORMATION: Portion of sequence repeated b times, wherein b
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (7)..(9)
<223> OTHER INFORMATION: Portion of sequence repeated c times, wherein c
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (10)..(12)
<223> OTHER INFORMATION: Portion of sequence repeated d times, wherein d
      is independently a number selected from 0, 1, 2, 3, 4, 5, 6, 7, 8,
```

-continued

```
       9, 10, 11, 12, 13, 14, 15, 16, 17, 18, 19, or 20
<220> FEATURE:
<221> NAME/KEY: REPEAT
<222> LOCATION: (13)..(15)
<223> OTHER INFORMATION: Portion of sequence repeated e times, wherein e
       is independently a number selected from 0, 1, 2, 3, 4, 5, 6, 7, 8,
       9, 10, 11, 12, 13, 14, 15, 16, 17, 18, 19, or 20

<400> SEQUENCE: 1

Gly Gly Ser Gly Ser Ser Gly Gly Gly Ser Ser Gly Gly Ser Gly
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Linker sequence

<400> SEQUENCE: 2

Gly Gly Ser Gly Gly Gly Gly Ser Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Epitope

<400> SEQUENCE: 3

Thr Ala Pro Asp Asn Leu Gly Tyr Ala
1               5

<210> SEQ ID NO 4
<211> LENGTH: 14
<212> TYPE: PRT
<213> ORGANISM: Artificial Sequence
<220> FEATURE:
<223> OTHER INFORMATION: Epitope

<400> SEQUENCE: 4

Cys Arg Pro Gly Trp Arg Gly Ala Ala Cys Asn Gln Lys Ile
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Epitope

<400> SEQUENCE: 5

Ser Val Tyr Asp Phe Phe Val Trp Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Epitope

<400> SEQUENCE: 6

Glu Gly Ser Arg Asn Gln Asp Trp Leu
1               5
```

-continued

```
<210> SEQ ID NO 7
<211> LENGTH: 8
<212> TYPE: PRT
<213> ORGANISM: Artificial Sequence
<220> FEATURE:
<223> OTHER INFORMATION: Epitope

<400> SEQUENCE: 7

Arg Gly Tyr Val Tyr Gln Gly Leu
1               5
```